(12) United States Patent
Schwartz et al.

(10) Patent No.: US 9,820,690 B1
(45) Date of Patent: Nov. 21, 2017

(54) ANALYTE DETECTION SYSTEM

(71) Applicant: Verily Life Sciences LLC, Mountain View, CA (US)

(72) Inventors: Jerrod Joseph Schwartz, San Francisco, CA (US); Vikram Singh Bajaj, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 196 days.

(21) Appl. No.: 14/333,140

(22) Filed: Jul. 16, 2014

(51) Int. Cl.
| | |
|---|---|
| *A61B 5/1455* | (2006.01) |
| *A61B 5/00* | (2006.01) |
| *A61B 5/1468* | (2006.01) |
| *A61B 5/055* | (2006.01) |

(52) U.S. Cl.
CPC .......... *A61B 5/4848* (2013.01); *A61B 5/055* (2013.01); *A61B 5/1455* (2013.01); *A61B 5/1468* (2013.01); *A61B 5/6802* (2013.01)

(58) Field of Classification Search
CPC .......... A61B 5/14532; A61B 5/14546; A61B 5/1486; A61B 5/14539; A61B 5/0031
See application file for complete search history.

(56) References Cited

U.S. PATENT DOCUMENTS

| | | | |
|---|---|---|---|
| 6,222,189 B1 * | 4/2001 | Misner ............... | A61B 5/14532 250/341.1 |
| 6,671,527 B2 | 12/2003 | Petersson et al. | |
| 7,214,190 B1 | 5/2007 | Wilson | |

(Continued)

FOREIGN PATENT DOCUMENTS

| | | |
|---|---|---|
| WO | 2011133925 A2 | 10/2011 |
| WO | 2011137514 A1 | 11/2011 |

(Continued)

OTHER PUBLICATIONS

Arruebo, Manuel et al., "Antibody-Conjugated Nanoparticles for Biomedical Applications," Journal of Nanomaterials, vol. 2009 (2009), Article ID 439389, 24 pages (available at http://dx.doi.org/10.1155/2009/439389).

(Continued)

*Primary Examiner* — Eric Winakur
(74) *Attorney, Agent, or Firm* — McDonnell Boehnen Hulbert & Berghoff LLP

(57) ABSTRACT

A wearable device includes a mount to mount the wearable device on a living body and a detector to detect an analyte response signal transmitted from tissue in the living body. The tissue contains a biologically active agent in an inactive state and functionalized particles. The biologically active agent can be converted to an active state that can affect a biological state of the living body. The functionalized particles are configured to bind with a target analyte, the presence or absence or concentration or abundance of which is correlated with the biological state. The analyte response signal is related to interaction of the target analyte with the functionalized particles. A source can apply directed energy into the tissue that is sufficient to convert the biologically active agent from the inactive state to the active state. A processor can determine a presence or absence or concentration or abundance of the analyte based on the analyte response signal.

22 Claims, 19 Drawing Sheets

(56) References Cited

U.S. PATENT DOCUMENTS

| | | | |
|---|---|---|---|
| 7,236,812 B1 | 6/2007 | Ballerstadt et al. | |
| 7,701,580 B2 | 4/2010 | Bassler et al. | |
| 7,763,856 B2 | 7/2010 | Kiesel et al. | |
| 7,817,254 B2 | 10/2010 | Hegyi et al. | |
| 7,817,276 B2 | 10/2010 | Kiesel et al. | |
| 7,844,314 B2 | 11/2010 | Al-Ali | |
| 7,894,068 B2 | 2/2011 | Bassler et al. | |
| 7,957,788 B2 | 6/2011 | Judd et al. | |
| 8,123,949 B2 | 4/2012 | Kiesel et al. | |
| 8,268,638 B2 | 9/2012 | Stein et al. | |
| 8,323,188 B2 * | 12/2012 | Tran | A61B 5/0022 600/300 |
| 8,344,731 B2 | 1/2013 | Lee | |
| 8,368,402 B2 | 2/2013 | Lee et al. | |
| 8,460,269 B2 | 6/2013 | Toma et al. | |
| 2004/0259270 A1 | 12/2004 | Wolf | |
| 2005/0054907 A1 * | 3/2005 | Page | A61B 5/0095 600/316 |
| 2006/0239919 A1 | 10/2006 | Wickline et al. | |
| 2007/0255122 A1 | 11/2007 | Vol et al. | |
| 2007/0270672 A1 | 11/2007 | Hayter | |
| 2008/0305046 A1 | 12/2008 | Hafezi-Moghadam | |
| 2009/0216300 A1 * | 8/2009 | Keltner | A61N 5/0601 607/89 |
| 2010/0049010 A1 | 2/2010 | Goldreich | |
| 2010/0204674 A1 | 8/2010 | Forbes et al. | |
| 2010/0259259 A1 | 10/2010 | Zahn et al. | |
| 2011/0027913 A1 | 2/2011 | Bau et al. | |
| 2011/0028803 A1 | 2/2011 | Ollmar | |
| 2011/0105866 A1 * | 5/2011 | Markle | A61B 5/14532 600/316 |
| 2011/0117028 A1 | 5/2011 | Zharov | |
| 2011/0166553 A1 * | 7/2011 | Holmes | A61B 5/0024 604/890.1 |
| 2011/0245693 A1 | 10/2011 | Hastings et al. | |
| 2011/0251476 A1 | 10/2011 | Gleich et al. | |
| 2011/0288234 A1 | 11/2011 | Pandey et al. | |
| 2013/0289520 A1 * | 10/2013 | Febvay | A61K 41/0057 604/501 |
| 2013/0296632 A1 * | 11/2013 | Whitmore | A61F 9/00 600/12 |
| 2014/0148425 A1 | 5/2014 | Bonnet | |

FOREIGN PATENT DOCUMENTS

| | | |
|---|---|---|
| WO | 2012052821 A1 | 4/2012 |
| WO | 2013016693 A2 | 1/2013 |

OTHER PUBLICATIONS

Cherry, Erika et al., "Simulation of Magnetic Particles in the Bloodstream for Magnetic Drug Targeting Applications," 8th International Conference on Multiphase Flow, ICMF 2013, May 26-31, 201, ICMF 2013, Jeju, Korea.

Shapiro, Benjamin "Towards Dynamic Control of Magnetic Fields to Focus Magnetic Carriers to Targets Deep Inside the Body," J Magn Magn Mater May 1, 2009; pp. 1-13.

Shao, Huilin et al, "Magnetic Nanoparticles for Biomedical NMR-based Diagnostics," Beilstein Journal of Nanotechnology, 2010, 1, 142-154.

Liu, Hao-Li et al, "Magnetic Resonance Monitoring of Focused Ultrasound/Magnetic Nanoparticle Targeting Delivery of Therapeutic Agents to the Brain," PNAS Early Edition, 2010, pp. 1-6.

Bariana, Manpreet, et al., "Radiofrequency-Triggered Release for On-Demand Delivery of Therapeutics from Titania Nanotube Drug-Eluting Implants", Nanomedicine, Dec. 20, 2013, pp. 1-12. (Abstract only).

Park, Kinam, "Programmed Sickle Cells for Targeted Delivery to Hypoxic Tumors", Journal of Controlled Release, 2013, vol. 171, p. 258.

Peiris, Pubudu, M., et al., "Enhanced Delivery of Chemotherapy to Tumors Using a Multicomponent Nanochain with Radio-Frequency-Tunable Drug Release", ACS Nano, Apr. 9, 2012, vol. 6(5), pp. 4157-4168. (Abstract only).

Pitt, William G., et al., "Ultrasonic Drug Delivery—A General Review", Expert Opin Drug Deliv., Nov. 2004, vol. 1(1), pp. 37-56.

Rapoport, N., "Ultrasound-Mediated Micellar Drug Delivery", Int J Hyperthermia, 2012, vol. 28(4), pp. 374-385 (Abstract only).

Wu, Yupeng, et al., "New Strategy for Controlled Release of Drugs. Potential Pinpoint Targeting with Multiresponsive Tetraaniline Diblock Polymer Vesicles: Site-Directed Burst Release with Voltage", ACS Appl. Mater. Interfaces, Jan. 22, 2014, vol. 6(3), pp. 1470-1480 (Abstract only).

Hoare, Todd, et al., "A Magnetically-Triggered Composite Membrane for On-Demand Drug Delivery", Nano. Lett., Oct. 2009, vol. 9(10), pp. 3651-3657.

"FDA's Office of Combination Products", KAI Research, Inc., (2008) accessed Jul. 7, 2014 from http://www.kai-research.com/focus/2011/nov/issue2.aspx.

* cited by examiner

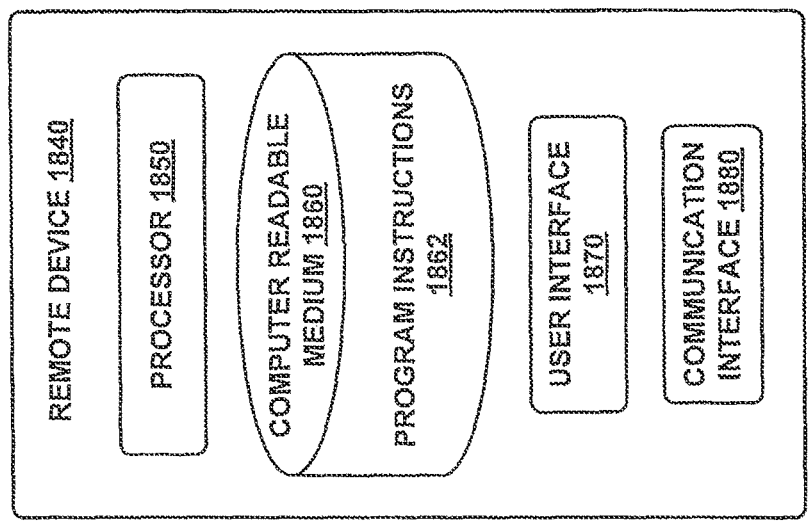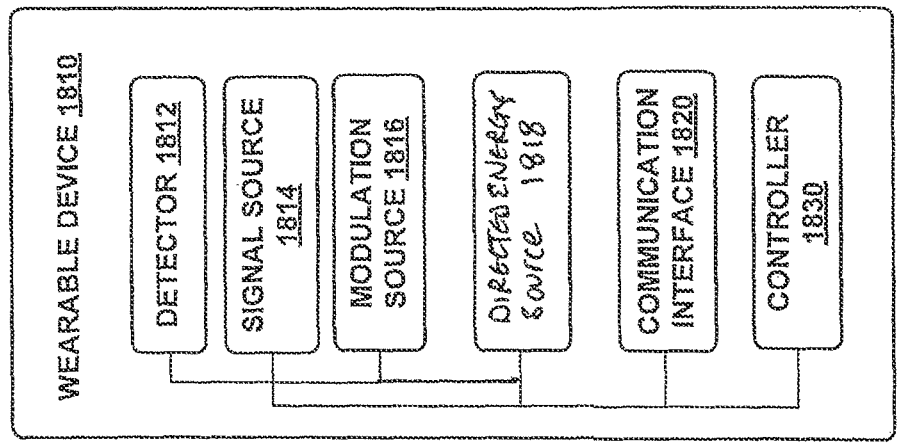
FIGURE 9C

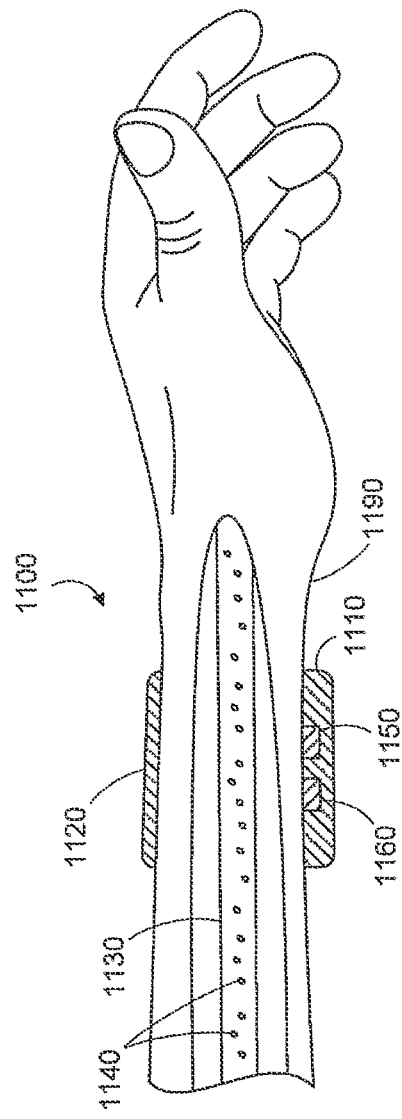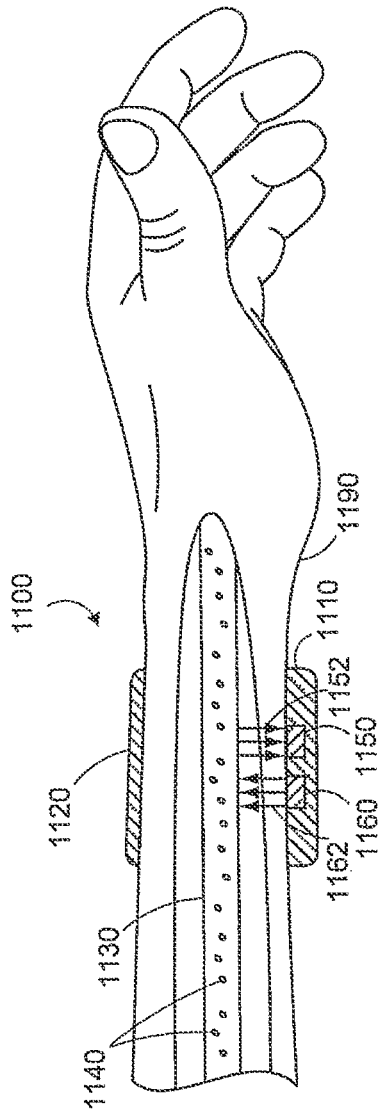

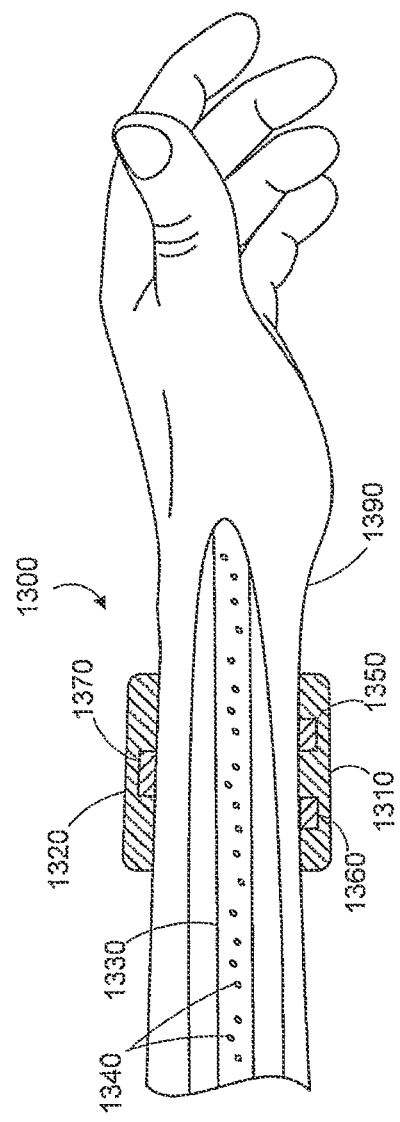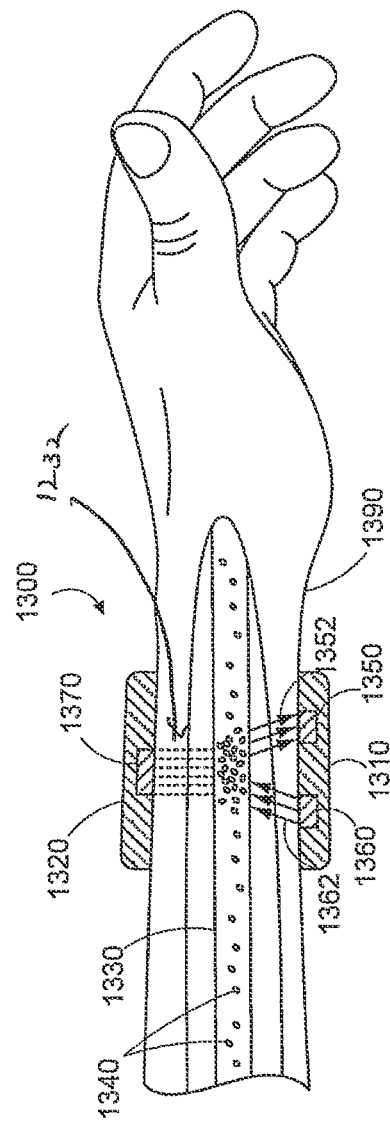

```
┌─────────────────────────────────────────────────┐
│ AUTOMATICALLY MEASURE, BY A WEARABLE DEVICE, A  │
│ PLURALITY OF PHYSIOLOGICAL PARAMETERS DURING EACH│
│ OF A PLURALITY OF MEASUREMENT PERIODS           │
└─────────────────────────────────────────────────┘
                        │
                        ▼  ─1410      1400
┌─────────────────────────────────────────────────┐
│ AUTOMATICALLY WIRELESSLY TRANSMIT BY THE         │
│ WEARABLE DEVICE DATA REPRESENTATIVE OF THE       │
│ PHYSIOLOGICAL PARAMETERS MEASURED DURING THAT    │
│ MEASUREMENT PERIOD, TO A SERVER                  │
└─────────────────────────────────────────────────┘
                        │  ─1420
                        ▼
┌─────────────────────────────────────────────────┐
│ DEVELOP A BASELINE PROFILE BASED ON THE DATA     │
│ TRANSMITTED BY THE WEARABLE DEVICE FOR THE       │
│ PLURALITY OF MEASUREMENT PERIODS                 │
└─────────────────────────────────────────────────┘
                        │  ─1430
                        ▼
┌─────────────────────────────────────────────────┐
│ INTRODUCE BIOLOGICALLY ACTIVE AGENT IN AN INACTIVE│
│ STATE AND APPLY DIRECTED ENERGY TO CONVERT THE   │
│ BIOLOGICALLY ACTIVE AGENT INTO AN ACTIVE STATE   │
└─────────────────────────────────────────────────┘
                        │  ─1435
                        ▼
┌─────────────────────────────────────────────────┐
│ RECEIVE FROM THE WEARABLE DEVICE ADDITIONAL DATA │
│ MEASURED DURING ONE OR MORE ADDITIONAL           │
│ MEASUREMENT PERIODS                              │
└─────────────────────────────────────────────────┘
                        │  ─1440
                        ▼
┌─────────────────────────────────────────────────┐
│ DETECT A CHANGE IN CONDITION BASED ON THE BASELINE│
│ PROFILE AND ADDITIONAL DATA                      │
└─────────────────────────────────────────────────┘
                        │  ─1450
                        ▼
┌─────────────────────────────────────────────────┐
│ GENERATE RECOMMENDATIONS BASED ON DETECTED       │
│ CHANGE IN CONDITION AND A CLINICAL PROTOCOL      │
└─────────────────────────────────────────────────┘
                        │  ─1460
                        ▼
┌─────────────────────────────────────────────────┐
│ RECEIVE DATA REGARDING PHYSIOLOGICAL PARAMETERS  │
│ MEASURED BY A PLURALITY OF WEARABLE DEVICES      │
└─────────────────────────────────────────────────┘
                           ─1470
```

FIGURE 14

ANALYTE DETECTION SYSTEM

BACKGROUND

Unless otherwise indicated herein, the materials described in this section are not prior art to the claims in this application and are not admitted to be prior art by inclusion in this section.

Controlled release of a drug by physical stimulus including application of directed energy such as light, magnetic field, acoustic wave, ultrasound, voltage, radiofrequency, and heat can have a marked impact on the treatment of a variety of medical conditions. However, it can be difficult to determine in real time whether or not a particular drug is effective for treating a medical condition in a patient and/or whether adjustments in the drug dosage regimen are needed. To assess efficacy of the drug and/or drug dosage regimen, it is desirable to monitor the health status of the patient including monitoring drug, drug metabolites, or other target analytes such as glucose. For instance, in the treatment of a diabetic patient, blood glucose levels can monitored to determine whether or not the patient is receiving sufficient amount of insulin, metformin, or other drug.

A number of scientific methods have been developed in the medical field to evaluate physiological conditions of a person by detecting and/or measuring one or more analytes in a person's blood or other bodily fluids or tissues. The one or more analytes could be any analytes that, when present in or absent from the blood, or present at a particular concentration, range of concentrations, or abundance may be indicative of a medical condition or health state of the person. The one or more analytes could include enzymes, reagents, hormones, proteins, cells, drugs, drug metabolites or other molecules, such as carbohydrates, e.g., glucose.

In a typical scenario, a person's blood is drawn and either sent to a lab or input into a handheld testing device, such as a glucose meter, where one or more tests are performed to measure various analyte levels and parameters in the blood. For most people, the blood tests are infrequent, and an abnormal analyte level indicative of a medical condition may not be identified until the next blood test is performed. Even in the case of relatively frequent blood testing, such as may be found with those with diabetes, who regularly draw blood to test for blood glucose concentration, those blood tests are typically performed when the user is awake, although the blood glucose levels (and potential variations in such levels) occurring during the night could provide important information to assist a physician in assessing that person's medical condition. Further, most known methods of analyte detection and analysis require the collection of blood or other bodily fluid samples, which may be inconvenient, invasive and require significant patient compliance.

Moreover, some blood analytes are particularly difficult to identify and quantify with conventional sensing techniques. For small or rarified analytes, such as circulating tumor cells, for example, only 1 such cell may be present in 10 mL of blood. Impractically large quantities of blood would have to be drawn or otherwise sampled and analyzed in order to catch such cells with statistical significance. Furthermore, for rapidly metathesizing tumor cells, the time needed to identify and quantify small number of tumor cells may further delay effective treatment of a cancer patient.

Methods for analyte detection and characterization often suffer from a low signal-to-noise ratio (SNR), since the signal obtained from the analyte (in general, a small object) is typically weak in comparison to the background. This can make discerning between target analytes present in the blood, versus other analytes, particles, and tissues, etc. present in the blood and elsewhere in the body can be very difficult, especially where the measurements are taken non-invasively from outside the body. This is particularly true with some methods of analyte characterization, such as optical methods, or where the target analytes are rare in the blood or are of a relatively small size. Accordingly, such measurements can be much more time consuming (if a large volume of blood must be analyzed), less sensitive, less specific and generally less informative on the whole. For example, with fluorescence detection techniques, it is often difficult to obtain highly sensitive measurements of a target analyte because other tissues, cells, and molecules in the body may have some inherent fluorescent properties, creating a high level of background noise.

SUMMARY

Some embodiments of the present disclosure provide a system including: (i) a wearable device comprising a mount configured to mount the wearable device on an external surface of a living body and a detector configured to detect an analyte response signal transmitted from tissue through the external surface, wherein the tissue contains a biologically active agent in an inactive state and functionalized particles, wherein the functionalized particles are configured to bind with one or more target analytes, wherein the biologically active agent can be converted from the inactive state to an active state, wherein the concentration or abundance of the one or more target analytes is correlated with a biological state of the living body that is affected by the biologically active agent when in the active state, and wherein the analyte response signal is related to interaction of the one or more target analytes with the functionalized particles; (ii) a source configured to apply directed energy into the tissue through the external surface, wherein the directed energy is sufficient to convert the biologically active agent from the inactive state to the active state; and (iii) a processor configured to determine concentration or abundance of the one or more target analytes based on the analyte response signal.

Further embodiments of the present disclosure provide a method including: (i) introducing a biologically active agent in an inactive state into a living body, wherein the biologically active agent can be converted to an active state that affects a biological state of the living body; (ii) introducing functionalized particles into the living body, wherein the functionalized particles are configured to bind with one or more target analytes, wherein the concentration or abundance of the one or more target analytes in the living body is correlated with the biological state of the living body; (iii) applying directed energy into the living body, wherein the directed energy is sufficient to convert the biologically active agent in the living body from the inactive state to the active state; (iv) detecting, by a wearable device mounted on an external surface of the living body, a signal transmitted from the living body, wherein the signal includes an analyte response signal that is related to binding of the one or more target analytes with the functionalized particles; and (v) determining the concentration or abundance of the one or more target analytes based on the analyte response signal. These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 9C is a functional block diagram of an example system including a wearable device and a remote device.

FIG. 11A is side partial cross-sectional view of a wrist-mounted device, while on a human wrist.

FIG. 11B is side partial cross-sectional view of a wrist-mounted device, while on a human wrist.

FIG. 13A is side partial cross-sectional view of a wrist-mounted device, while on a human wrist.

FIG. 13B is side partial cross-sectional view of a wrist-mounted device, while on a human wrist.

FIG. 14 is a flowchart of an example method for using a wearable device to take real-time, high-density, non-invasive, in vivo measurements of physiological parameters.

DETAILED DESCRIPTION

Figure 1:
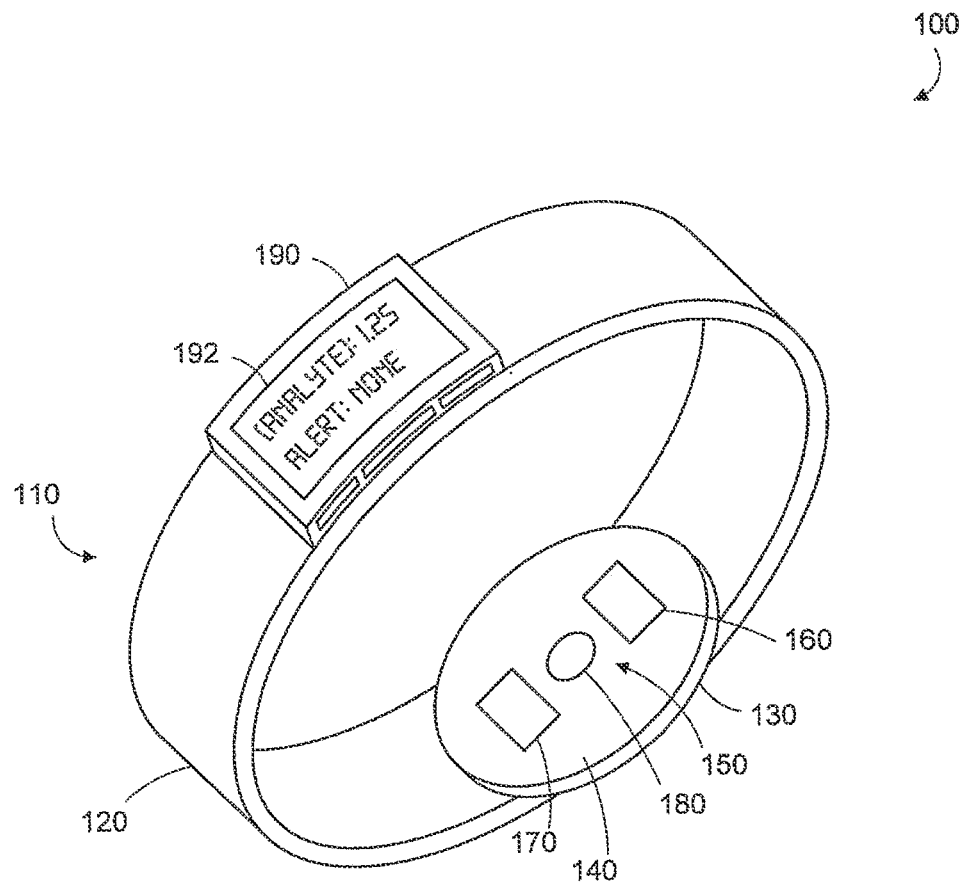
FIG. 1 is a perspective view of an example wearable device.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body, it is contemplated that the disclosed methods, systems and devices may be used in any environment where non-invasive detection of an analyte is desired. The environment may be any living or non-living body or a portion thereof, a fluid conduit, a fluid reservoir, etc. For example, one of skill in the art will recognize that the embodiments disclosed herein may be used to sense analytes present in a water system. Moreover, while the present disclosure describes embodiments for use in vivo, one of skill in the art will also recognize that in vitro applications are possible as well. Accordingly, the environment may also include a test tube or other vessel for holding a fluid.

I. OVERVIEW

Controlled release of a drug or biologically active agent in active form by application of directed energy such as electromagnetic radiation, e.g., light, magnetism, or electrical voltage or current; acoustic energy, e.g., ultrasound or radiofrequency; and heat energy can have a marked impact on the treatment of a variety of medical conditions. A drug, also referred to as a biologically active agent or a bioactive agent, may be in an inactive state such as being associated with a carrier such as a liposome, micelle, nanoparticle, reservoir or a nanocage; may be in pro-drug form, or both. Upon application of a directed energy field, the bioactive agent converts from an inactive state to an active state. The directed energy can be applied as a single pulse or in a pre-determined series of one or more pulses, each pulse of a pre-determined duration, which in turn controls the rate of conversion or release of the bioactive agent in its active state over time. In an example embodiment, the bioactive agent in inactive form is introduced to a patient and an applied energy field of sufficient strength from an external source is applied to at least a portion of the patient's body to trigger the release of the bioactive agent in its active state. The drug carrier can assume a variety of forms including a composition of matter designed for a one-time release, e.g., liposome, miscelle or nanoparticle. In another embodiment, a refillable device, reservoir, nanocage, or chamber containing the bioactive agent in an active state may be implanted in the patient, and the applied directed energy would trigger the release of the bioactive agent in active form from the device into the patient. The carrier for on-demand drug delivery can safely contain a desired quantity of drug and release little or no drug in the "off" state and be switchable to the "on" state without mechanically disrupting the device. Furthermore, the carrier can be triggered non-invasively to release a consistent dosage demanded by the patient (e.g., local pain relief) or as prescribed by a physician (e.g., insulin delivery, chemotherapy or systemic pain relief). The efficacy of the drug dosage regimen in treating a medical condition or in maintaining a health state can be monitored by detecting and measuring a physiological parameter including one or more target analytes that may be present or absent in a patient and the drug dosing regimen can be adjusted or changed according to patient needs.

A diagnostic system can non-invasively detect and measure a plurality of physiological parameters of a person, which can include any parameters that may relate to the person's health. For example, the system could include sensors for measuring blood pressure, pulse rate, skin temperature, etc. At least some of the physiological parameters may be obtained by the system non-invasively detecting and/or measuring one or more analytes in blood circulating in subsurface vasculature. The one or more analytes could be any analytes that, when present in or absent from the blood, or present at a particular concentration or range of concentrations, may be indicative of a medical condition or health of the person. For example, the one or more analytes could include enzymes, hormones, proteins, cells or other molecules.

In an example embodiment, the system obtains at least some of the health-related information by detecting the binding or interaction of a clinically-relevant analyte to or with particles, for example, microparticles or nanoparticles, introduced into a lumen of the subsurface vasculature that have been functionalized with a receptor that has a specific affinity to bind to or interact with the specific analyte. The term "binding" is understood in its broadest sense to also include a detectable interaction between the clinically relevant analyte and the functionalized particles. The functionalized particles can be introduced into the person's blood stream by injection, ingestion, inhalation, transdermally, or in some other manner.

The particles can be functionalized by covalently or otherwise attaching or associating a receptor that specifically binds or otherwise interacts with a particular clinically-relevant analyte. The functionalized receptor can be an antibody, peptide, nucleic acid, phage, bacteria, virus, aptamer or any other molecule with a defined affinity for a target analyte. Additionally or alternatively, the receptor may be inherent to the particle itself. For example, the particle itself may be a virus or a phage with an inherent affinity for certain analytes. Other compounds or molecules, such as fluorophores or autofluorescent or luminescent markers or non-optical contrast agents (e.g. acoustic impedance contrast, RF contrast and the like), which may assist in interrogating the particles in vivo, may also be attached to the particles.

The particles can have a diameter that is less than about 20 micrometers. In some embodiments, the particles have a diameter on the order of about 10 nanometers to 1 micrometer. In further embodiments, small particles on the order of 10-100 nanometers in diameter may be assembled to form a larger "clusters" or "assemblies on the order of 1-10 micrometers. Those of skill in the art will understand a "particle" in its broadest sense and that it may take the form of any fabricated material, a molecule, cryptophan, a virus, a phage, etc. Further, a particle may be of any shape, for example, spheres, rods, non-symmetrical shapes, etc.

In some examples, the particles may also be magnetic and can be formed from a paramagnetic, super-paramagnetic or ferromagnetic material or any other material that responds to a magnetic field. Alternatively, the particles may also be made of non-magnetic materials such as polystyrene. Where magnetic particles are used, the system may include a magnet that can direct into the portion of subsurface vasculature a magnetic field that is sufficient to manipulate functionalized magnetic particles in a lumen of that portion of subsurface vasculature, for example, to collect or slow down in a certain area. However, measurements may be taken without localized "collection" of the functionalized particles. The system may be configured to activate the magnetic periodically, such as at certain times of the day (e.g., every hour).

The system may include a source of directed energy configured to direct energy into tissue through the external tissue that can penetrate into a portion of subsurface vasculature, or another body system. The directed energy source may be in the form of an external device that is configured to generate energy on demand or automatically and at levels that is benign to the patient such as electromagnetic, magnetic, optic, acoustic, thermal, mechanical, electrical and results in the controlled release of an bioactive compound in an active state from an inactive state. In some cases, the source may be a component of a wearable device as discussed below.

In one embodiment, the application of directed energy results in the release of the bioactive drug at a controlled rate over time and/or at a rate determined using a detected level of bioavailable drug or some other state of the human body (e.g., glucose level). In one example, the directed energy is a radiofrequency signal of significant power to rapidly heat drug carriers such as metallic nanoparticle compositions encapsulating drugs, thus rupturing the carrier to release the drug. In another example, the directed energy is light energy such as near infrared energy which can penetrate the subsurface vasculature and tissue and release drug from light sensitive carrier compositions. In another example, the directed energy can be ultrasound which causes cavitation of the liquid medium in contact with the drug carriers, resulting in release of the drug from the carrier.

The system may further include one or more data collection systems for interrogating, in a non-invasive manner, the functionalized particles present in a lumen of the subsurface vasculature in a particular local area. In one example, the system includes a detector configured to detect a response signal transmitted from a portion of subsurface vasculature. The response signal can include both an analyte response signal, which can be related to the interaction of the one or more target analytes with the functionalized particles, and a background noise signal. For example, the functionalized particles may include a chemiluminescent marker configured to produce a response signal in the form of luminescence radiation produced in response to a chemical reaction initiated, at least in part, to the binding of the target analyte to the particle.

In some examples, the system may also include an interrogating signal source for transmitting an interrogating signal that can penetrate into a portion of subsurface vasculature, or another body system, and a detector for detecting a response signal that is transmitted from the portion of subsurface vasculature, or other body system, in response to the interrogating signal. The interrogating signal can be any kind of signal that is benign to the patient, such as electromagnetic, magnetic, optic, acoustic, thermal, mechanical, electric and results in a response signal that can be used to measure a physiological parameter or, more particularly, that can detect the binding or interaction of the clinically-relevant analyte to the functionalized particles. In one example, the interrogating signal is a radio frequency (RF) signal and the response signal is a magnetic resonance signal, such as nuclear magnetic resonance (NMR). In another example, where the functionalized particles include a fluorophore, the interrogating signal is an optical signal with a wavelength that can excite the fluorophore and penetrate the skin or other tissue and subsurface vasculature (e.g., a wavelength in the range of about 500 to about 1000 nanometers), and the response signal is fluorescence radiation from the fluorophore that can penetrate the subsurface vasculature and tissue to reach the detector. In another example, where the functionalized particles include an electrically conductive material or a magnetically lossy material, the interrogation signal may be a time-varying magnetic field or a radio frequency (RF) electromagnetic signal, with sufficient signal power to rapidly heat the particles. The response signal may be an acoustic emission from the particles, caused by rapid thermal expansion of the particles, or caused by cavitation of the liquid medium in contact with the particles. As described above, in some cases, an interrogating signal may not be necessary to produce an analyte response signal. Relative to the directed energy, the interrogation signal may be selected such that it is different from the directed energy type or that its strength is not sufficient to trigger unintended conversion of the biologically active agent into its active state from an inactive state.

Additionally, the system may further include a modulation source configured to modulate the analyte response signal. The modulation source can be configured to modulate the analyte response signal differently than the background noise signal. To this end, the modulation may help to discern between the target analyte and, essentially, everything else in the body by, for example, increasing the signal-to-noise ratio. Generally, the modulation may include any spatial, temporal, spectral, thermal, magnetic, mechanical, electrical, acoustic, chemical, or electrochemical, etc. modulation technique or any combination thereof.

In some scenarios, it may also be useful to detect and distinguish both the analyte response signal—related to functionalized particles bound to or interacting with target analyte(s)—and an "unbound" particle signal—related to functionalized particles not bound to or interacting with target analyte(s). For example, in some measurement or characterization schemes, it may be useful or necessary to determine the percentage of functionalized particles introduced into the body that have bound to the target analyte. In such cases, the modulation source may be configured to modulate the analyte response signal differently than the unbound particle signal.

Data collected by the detector may be sent to a processor for analysis. The processor may be configured to non-invasively detect the one or more target analytes by differentiating the analyte response signal from the background noise signal based, at least in part, on the modulation. In some cases, the processor may further be configured to differentiate the analyte response signal from the unbound particle signal. Further, the processor may be configured to determine the concentration of a particular target analyte in the blood from, at least in part, the analyte response signal. In some cases, the processor may be further configured to control the rate of conversion of the biologically active agent to the active state, to assess the effect of the biologically active agent on the state of the living body, and/or to trigger the source to apply the directed energy, based on the determined presence or absence or concentration or abundanceof the target analyte. The detection and concentration data processed by the processor may be communicated to the patient, transmitted to medical or clinical personnel, locally stored or transmitted to a remote server, the cloud, and/or any other system where the data may be stored or accessed at a later time.

The processor may be located on an external reader, which may be provided as an external body-mounted device, such as a necklace, wristwatch, eyeglasses, a mobile phone, a handheld or personal computing device or some combination thereof. Data collected by the detector may be transmitted to the external reader via a communication interface. Control electronics can wirelessly communicate the data to the external reader by modifying the impedance of an antenna in communication with the detector so as to characteristically modify the backscatter from the antenna. In some examples, the external reader can operate to intermittently interrogate the detector to provide a reading by radiating sufficient radiation to power the detector to obtain a measurement and communicate the result. In this way, the external reader can acquire a series of analyte identification and concentration measurements over time without continuously powering the detector and/or processor. The processor may also be provided at another location distal to the detector, and the detector data is communicated to the processor via a wired connection, a memory card, a USB device or other known method. Alternatively, the processor may be located proximal to the detector and may be configured to locally analyze the data that it collects and then transmit the results of the analysis to an external reader or server.

The external reader may include a user interface, or may further transmit the collected data to a device with a user interface that can indicate the results of the data analysis. In this way, the person wearing, holding or viewing the device can be made aware of the nutritional analysis and/or potential medical conditions. The external reader may also be configured to produce an auditory or tactile (vibration) response to alert the patient of a medical condition. Further, the external reader may also be configured to receive information from the patient regarding his/her health state, wellness state, activity state, nutrition intake and the like, as additional input information to the processor. For example, the user may input a health or wellness state, such as, experiencing migraine symptoms, jittery, racing heart, upset stomach, feeling tired, activity state including types and duration of physical activity nutrition intake including meal timing and composition, and other parameters including body weight, medication intake, quality of sleep, stress level, personal care products used, environmental conditions, social activity, etc. Further, the reader may also receive signals from one or more other detectors, such as a pedometer, heart rate sensor, blood pressure sensor, blood oxygen saturation level, body temperature, GPS or other location or positioning sensors, microphone, light sensor, etc.

The system may be configured to obtain data during pre-set measurement periods or in response to a prompt. For example, the system may be configured to operate the detector and collect data once an hour. In other examples, the system may be configured to operate the detector in response to a prompt, such as a manual input by the patient or a physician. The system may also be configured to obtain data in response to an internal or external event or combination of events, such as during or after physical activity, at rest, at high pulse rates, high or low blood pressures, cold or hot weather conditions, etc. In other examples, the system could operate the detector more frequently or less frequently, or the system could measure some analytes more frequently than others.

Data collected by the system may be used to notify the patient of, as described above, analyte levels or of an existing or imminent medical emergency. In some examples, the data may be used to develop an individual baseline profile for the patient. The baseline profile may include patterns for how one or more of the patient's analyte levels typically change over time, such as during the course of a day, a week, or a month, or in response to consumption of a particular type of food/drug. The baseline profile, in essence, may establish "normal" levels of the measured analytes for the patient. Additional data, collected over additional measurement periods, may be compared to the baseline profile. If the additional data is consistent with the patterns embodied in the baseline profile, it may be determined that the patient's condition has not changed. On the other hand, if the additional data deviates from the patterns embodied in the baseline profile, it may be determined that the patient's condition has changed. The change in condition could, for example, indicate that the patient has developed a disease, disorder, or other adverse medical condition as a result of drug treatment or may be at risk for a severe medical condition in the near future. Further, the change in condition could further indicate a change in the patient's eating habits, either positively or negatively, which could be of interest to medical personnel. Further, the patient's baseline and deviations from the baseline can be compared to baseline and deviation data collected from a population of wearers of the devices.

When a change in condition is detected, a clinical protocol may be consulted to generate one or more recommendations that are appropriate for the patient's change in condition. For example, it may be recommended that the patient inject himself/herself with insulin, change his/her diet, take a particular medication or supplement, stop drug treatment, schedule an appointment with a medical professional, get a specific medical test, go to the hospital to seek immediate medical attention, abstain from certain activities, etc. The clinical protocol may be developed based, at least in part, on correlations between analyte concentration and health state derived by the server, any known health information or medical history of the patient, and/or on recognized standards of care in the medical field. The one or more recommendations may then be transmitted to the external reader for communication to the user via the user interface.

Correlations may be derived between the analyte concentration(s) measured by the system and the health state reported by the patient. For example, analysis of the analyte data and the health state data may reveal that the patient has experienced certain adverse health conditions, such as a migraine or a heart attack, when an analyte reaches a certain concentration. This correlation data may be used to generate recommendations for the patient, or to develop a clinical protocol. Blood analysis may be complemented with other physiological measurements such as blood pressure, heart rate, body temperature etc., in order to add to or enhance these correlations.

Further, data collected from a plurality of patients, including both the analyte measurements and the indications of health state, may be used to develop one or more clinical protocols used by the server to generate recommendations and/or used by medical professionals to provide medical care and advice to their patients. This data may further be used to recognize correlations between blood analytes and health conditions among the population. Health professionals may further use this data to diagnose and prevent illness and disease, prevent serious clinical events in the population, and to update clinical protocols, courses of treatment, and the standard of care.

The above described system may be implemented as a wearable device. The term "wearable device," as used in this disclosure, refers to any device that is capable of being worn at, on or in proximity to a body surface, such as a wrist, ankle, waist, chest, ear, eye or other body part. In order to take in vivo measurements in a non-invasive manner from outside of the body, the wearable device may be positioned on a portion of the body where subsurface vasculature is easily observable, the qualification of which will depend on the type of detection system used. The device may be placed in close proximity to the skin or tissue, but need not be touching or in intimate contact therewith. A mount, such as a belt, wristband, ankle band, headband, etc. can be provided to mount the device at, on or in proximity to the body surface. The mount may prevent the wearable device from moving relative to the body to reduce measurement error and noise. Further, the mount may be an adhesive substrate for adhering the wearable device to the body of a wearer. The detector, directed energy source, modulation source, interrogation signal source (if applicable) and, in some examples, the processor, may be provided on the wearable device. In other embodiments, the above described system may be implemented as a stationary measurement device to which a user must be brought into contact or proximity with or as a device that may be temporarily placed or held against a body surface during one or more measurement periods.

It should be understood that the above embodiments, and other embodiments described herein, are provided for explanatory purposes, and are not intended to be limiting.

Further, the term "medical condition" as used herein should be understood broadly to include any disease, illness, disorder, injury, condition or impairment—e.g., physiologic, psychological, cardiac, vascular, orthopedic, visual, speech, or hearing—or any situation requiring medical attention.

II. EXAMPLE DRUG CARRIERS AND DIRECTED ENERGY SOURCES

Controlled release of a drug in an active state from an inactive state by the application of directed energy can have a marked impact on the treatment of a variety of medical conditions. The directed energy includes any suitable energy form including light, magnetic field, acoustic wave, ultrasound, voltage, radiofrequency, and heat. In one embodiment, the applied energy field from an external source would be of a strength that is sufficient to trigger the conversion of a drug from an inactive state to an active state but benign to the patient. For instance, the directed energy would be sufficient to release of the drug from a drug carrier on demand. The drug carrier can assume a variety of foims including a composition of matter designed for a one-time release, e.g., liposome, miscelles, or nanoparticles.

Alternatively, the drug carrier may be an implantable refillable device, reservoir, nanocage or chamber. The carrier can safely contain a desired quantity of drug and release little or no drug in the "off" state and be switchable to the "on" state without mechanically disrupting the device. Furthermore, the carrier can be triggered non-invasively to release a consistent dosage demanded by the patient (e.g., local pain relief) or prescribed by a physician (e.g., insulin delivery, chemotherapy or systemic pain relief). Furthermore, the drug dosing levels can be adjusted according to patient needs.

Representative drug delivery devices include, without limitation, radiofrequency-activated implanted microchips including refillable reservoirs; ferrofluid-loaded polymer sheets, liposomes, microspheres, microcapsules, and nanospheres which can be activated by magnetic induction; heat triggerable hydrogels, gel-based microparticles or nanoparticles and surface-grafted polymers based on thermosensitive poly(N-isopropylacrylamide)(PNIPAM); near-IR responsive nanoparticles embedded in PNIPAM; radiofrequency (RF) triggered release of a nanotube including gold nanoparticles, drug, and micelles where the gold nanoparticles function as an RF energy transducer; RF release of drug from a linear assembly of iron oxide nanoparticles linked to a drug loaded liposome; light activated sickle red blood cells; ultrasound triggerable liposomes and micelles having encapsulated drug where cavitation of gas bubbles causes the disruption of the liposome/micelles and release of the drug; light triggerable nanoparticles having photosensitizers; and other triggerable carrier materials or combinations of such materials such as liposomes, microspheres, microcapsules, etc.

By using an energy field directed into the human body from an external source or device, the bioavailability of the drug or other bioactive agent in the human body can be controlled. For instance, a pre-determined drug dose in micelles or liposomes can be introduced into the human body and made into an active bioavailable state using directed energy at a controlled rate over time and/or at a rate determined using a detected level of bioavailable drug, drug metabolite, or some other state of the human body, e.g., glucose level. The carrier, e.g., liposomes and nanomaterials, encasing the drug are sufficiently small so that it can pass through capillaries and can bind to specific targets such as organs, cancer cells, etc. Once at the target, the device releases their drug load in active form in response to the directed energy such as ultrasound waves or increased temperature or oscillating magnetic fields. The directed energy can be administered as a single pulse of pre-determined strength and duration or as multiple on-off cycles of directed energy in the form of one or more pulses of a pre-desired strength and duration in order to produce and/or maintain a desired level of bioavailable drug or other state of the human body.

In another embodiment, the applied energy field would be of a strength sufficient to trigger the change of a bioactive agent from an inactive state into an active state. For instance, a drug labeled with an agent such as a photosensitizer or a carrier associated a photosensitizer can be released from the agent or carrier by being exposed to the directed energy. Upon exposure to directed light energy (e.g., ultraviolet, visible, infrared, near infrared, far infrared, X-ray, two-photon excitation, etc.), the photosensitizer can generate a reactive oxygen species which converts the drug from an inactive state into an active form. Alternatively, the reactive oxygen species can rupture the carrier, e.g., micelle, releasing active drug. In another aspect, the inactive drug, e.g., a ruthenium-based anticancer prodrug, can include light or heat-sensitive links, bonds or functionalities such as reactive chemical groups which upon directed exposure to light or heat can generate a drug in active form.

The directed energy can be produced from an external source, e.g., a radiofrequency transmitter device or UV lamp, that can generate energy such as electromagnetic, magnetic, optic, acoustic, thermal, mechanical, or electrical at levels that are benign to the patient and result in the controlled release of an bioactive agent in an active form from an inactive form. For instance, release of a drug in an active state from a carrier, e.g., nanoparticle encapsulate, nanocage or device, e.g., microchip reservoir, or through direct interaction of a pro-drug with the directed energy to produce a bioactive agent (drug) when in the active state. The directed energy can penetrate into a portion of subsurface vasculature, or another body system. In one embodiment, the application of directed energy results in the release of the bioactive drug in the active state at a controlled rate over time and/or at a rate determined using a detected level of bioavailable drug or some other state of the human body (e.g., glucose level). In one example, the directed energy is a radio frequency signal of significant power to rapidly heat drug carriers such as metallic nanoparticle compositions encapsulating drugs, thus rupturing the carrier to release the drug. In another example, the directed energy is light energy such as near infrared energy which can penetrate the subsurface vasculature and tissue and release drug from light sensitive carrier compositions. In another example, the directed energy can be ultrasound which causes cavitation of the liquid medium in contact with the drug carriers, resulting in release of the drug from the carrier. Ultimately, the type of directed energy that is used to activate the biologically active agent may be dictated, to some extent, by the characteristics of the biologically active agent and/or the carrier.

III. EXAMPLE WEARABLE DEVICES

A wearable device 100 can automatically measure a plurality of physiological parameters of a person wearing the device. The term "wearable device," as used in this disclosure, refers to any device that is capable of being worn at, on or in proximity to a body surface, such as a wrist, ankle, waist, chest, or other body part. In order to take in vivo measurements in a non-invasive manner from outside of the body, the wearable device may be positioned on a portion of the body where subsurface vasculature is easily observable, the qualification of which will depend on the type of detection system used. The device may be placed in close proximity to the skin or tissue, but need not be touching or in intimate contact therewith. A mount 110, such as a belt, wristband, ankle band, etc. can be provided to mount the device at, on or in proximity to the body surface. The mount 110 may prevent the wearable device from moving relative to the body to reduce measurement error and noise. In one example, shown in FIG. 1, the mount 110, may take the form of a strap or band 120 that can be worn around a part of the body. Further, the mount 110 may be an adhesive substrate for adhering the wearable device 100 to the body of a wearer.

A measurement platform 130 is disposed on the mount 110 such that it can be positioned on the body where subsurface vasculature is easily observable. An inner face 140 of the measurement platform is intended to be mounted facing to the body surface. The measurement platform 130 may house the data collection system 150, which may include at least one detector 160 for detecting at least one physiological parameter, which could include any parameters that may relate to the health of the person wearing the wearable device. For example, the detector 160 could be configured to measure blood pressure, pulse rate, respiration rate, skin temperature, etc. At least one of the detectors 160 is configured to non-invasively measure one or more analytes in blood circulating in subsurface vasculature proximate to the wearable device. In a non-exhaustive list, detector 160 may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor. The components of the data collection system 150 may be miniaturized so that the wearable device may be worn on the body without significantly interfering with the wearer's usual activities.

In some examples, the data collection system 150 further includes a signal source 170 for transmitting an interrogating signal that can penetrate the wearer's skin into the portion of subsurface vasculature, for example, into a lumen of the subsurface vasculature. The interrogating signal can be any kind of signal that is benign to the wearer, such as electromagnetic, magnetic, optic, acoustic, thermal, mechanical, and results in a response signal that can be used to measure a physiological parameter or, more particularly, that can detect the binding of the clinically-relevant analyte to the functionalized particles. In one example, the interrogating signal is an electromagnetic pulse (e.g., a radio frequency (RF) pulse) and the response signal is a magnetic resonance signal, such as nuclear magnetic resonance (NMR). In another example, the interrogating signal is a time-varying magnetic field, and the response signal is an externally-detectable physical motion due to the time-varying magnetic field. The time-varying magnetic field modulates the particles by physical motion in a manner different from the background, making them easier to detect. In a further example, the interrogating signal is an electromagnetic radiation signal. In particular, the interrogating signal may be electromagnetic radiation having a wavelength between about 400 nanometers and about 1600 nanometers. The interrogating signal may, more particularly, comprise electromagnetic radiation having a wavelength between about 500 nanometers and about 1000 nanometers. In some examples, the functionalized particles include a fluorophore. The interrogating signal may therefore be an electromagnetic radiation signal with a wavelength that can excite the fluorophore and penetrate the skin or other tissue and subsurface vasculature (e.g., a wavelength in the range of about 500 to about 1000 nanometers), and the response signal is fluorescence radiation from the fluorophore that can penetrate the subsurface vasculature and tissue to reach the detector.

In some cases, an interrogating signal is not necessary to measure one or more of the physiological parameters and, therefore, the wearable device 100 may not include a signal source 170. For example, the functionalized particles include an autofluorescent or luminescent marker, such as a fluorophore, that will automatically emit a response signal indicative of the binding of the clinically-relevant analyte to the functionalized particles, without the need for an interrogating signal or other external stimulus. In some examples, the functionalized particles may include a chemiluminescent marker configured to produce a response signal in the form of luminescence radiation produced in response to a chemical reaction initiated, at least in part, to the binding of the target analyte to the particle.

A collection magnet 180 may also be included in the data collection system 150. In such embodiments, the functionalized particles may also be made of or be functionalized with magnetic materials, such as ferromagnetic, paramagnetic, super-paramagnetic, or any other material that responds to a magnetic field. The collection magnet 180 is configured to direct a magnetic field into the portion of subsurface vasculature that is sufficient to cause functionalized magnetic particles to collect in a lumen of that portion of subsurface vasculature. The magnet may be an electromagnet that may be turned on during measurement periods and turned off when a measurement period is complete so as to allow the magnetic particles to disperse through the vasculature.

The wearable device 100 may also include a user interface 190 via which the wearer of the device may receive one or more recommendations or alerts generated either from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 190 may include a display 192 where a visual indication of the alert or recommendation may be displayed. The display 192 may further be configured to provide an indication of the measured physiological parameters, for instance, the concentrations of certain blood analytes being measured. In some cases, the wearable device may include a source of directed energy (not shown) such as electromagnetic radiation, acoustic energy and heat for triggering the release of a biologically active agent from in inactive state to an active state in order to treat a medical condition or to maintain a particular health state.

The wearable device may, in some cases, also include a modulation source. The signal-to-noise ratio (SNR) in an analyte detection system, such as any of those described above, may be increased by modulating the analyte response signal transmitted from the subsurface vasculature (or other body system) with respect to the background signal and, in some cases, an unbound particle response signal. Such modulation can increase the system's sensitivity and ability to discern between target analytes present in the blood or other bodily fluids, versus other analytes, particles, cells, molecules, blood components, bone and tissues, etc. This can be particularly valuable with some methods of analyte characterization, such as optical methods, or where the target analytes are rare in the blood or are of a relatively small size and with fluorescence detection techniques, which can often suffer from low resolution because other tissues, cells, and molecules in the body may have some inherent fluorescent properties, creating a high level of background noise.

The modulation source may apply a modulation, configured to modulate the response signal, to the portion of the body. Specifically, the modulation source may be configured to modulate the analyte response signal differently from a background signal. The background signal may include any signal transmitted from something other than what the system is monitoring, i.e., the target analyte(s). In some examples, the background signal may be generated by other molecules, cells, or particles in the blood or other bodily fluids; tissue, such as skin, veins, muscle, etc.; bone; or other objects present in the wearer's body. A background signal may be generated by excitation of these objects from the interrogating signal, such as by generating an autofluorescence signal, or due to some inherent property of these objects, such as, chemiluminescence, etc.

In some examples, the modulation source may be configured to modulate the analyte response signal (transmitted from bound particles) differently than the unbound particle signal (transmitted from particles that are not bound or otherwise interacting with the target analyte(s)), such that the analyte response signal may be differentiated from the unbound particle signal. Such differentiation may be used to determine the number or percentage of particles bound to or interacting with the target analyte(s), which may be used to determine a concentration of the target analyte(s) in the blood or other bodily fluid, to determine if and to what extent the particles are being cleared from the body, etc.

The modulation source may include any means for modulating the response signal. In some cases, the analyte response signal may be modulated differently than the background signal, and in other cases the analyte response signal may be modulated differently than the unbound particle signal, or both. For example, the modulation source may be configured to alter the spatial, optical magnetic, electric, acoustic, and/or physical properties of the bound particles. The modulation source may be a physical construct or it may be a signal or energy applied to the body, or a combination thereof. Accordingly, the modulation may include spatial, temporal, spectral, thermal, magnetic, optical, mechanical, electrical, acoustic, chemical, or electrochemical type of modulation or any combination thereof.

Figure 2A:
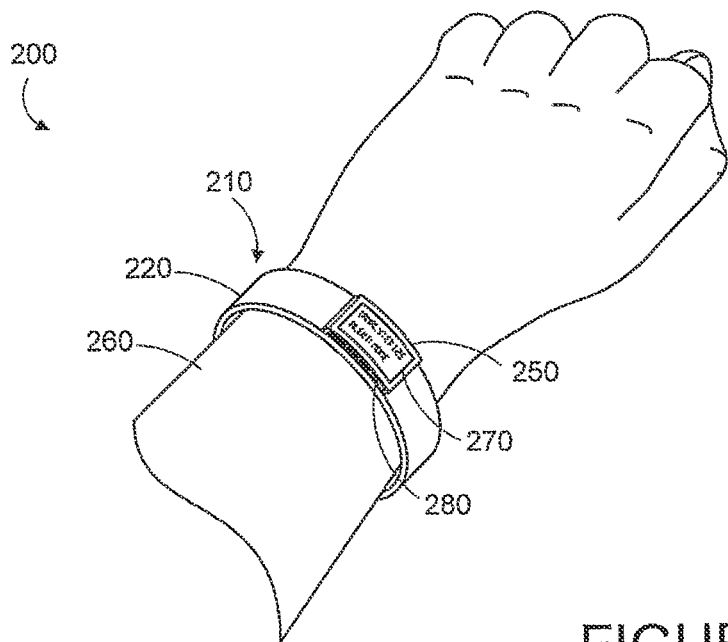
FIG. 2A is a perspective top view of an example wrist-mounted device, when mounted on a wearer's wrist.
Figure 2B:
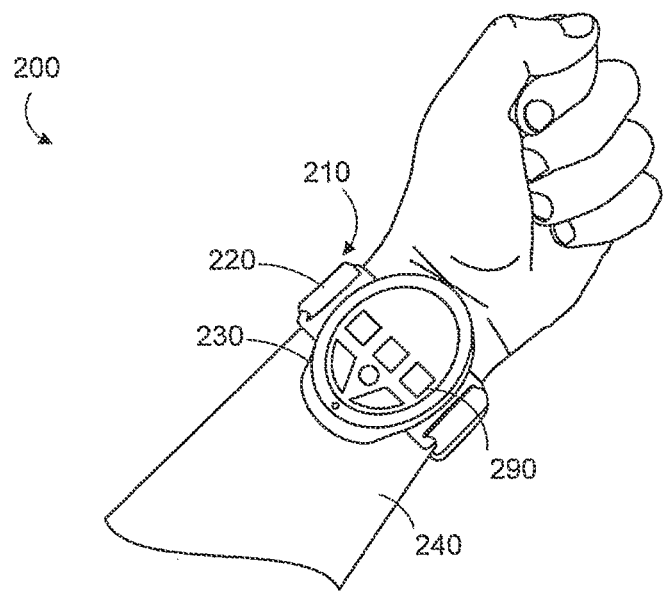
FIG. 2B is a perspective bottom view of an example wrist-mounted device shown in FIG. 2A, when mounted on a wearer's wrist.

In one example, the wearable device is provided as a wrist-mounted device, as shown in FIGS. 2A, 2B, 3A-3C, 4A, 5B, 6 and 7. The wrist-mounted device may be mounted to the wrist of a living subject with a wristband or cuff, similar to a watch or bracelet. As shown in FIGS. 2A and 2B, the wrist mounted device 200 may include a mount 210 in the form of a wristband 220, a measurement platform 230 positioned on the anterior side 240 of the wearer's wrist, and a user interface 250 positioned on the posterior side 260 of the wearer's wrist. The wearer of the device may receive, via the user interface 250, one or more recommendations or alerts generated either from a remote server or other remote computing device, or alerts from the measurement platform. Such a configuration may be perceived as natural for the wearer of the device in that it is common for the posterior side 260 of the wrist to be observed, such as the act of checking a wrist-watch. Accordingly, the wearer may easily view a display 270 on the user interface. Further, the measurement platform 230 may be located on the anterior side 240 of the wearer's wrist where the subsurface vasculature may be readily observable. However, other configurations are contemplated.

The display 270 may be configured to display a visual indication of the alert or recommendation and/or an indication of the measured physiological parameters, for instance, the concentrations of certain blood analytes being measured. Further, the user interface 250 may include one or more buttons 280 for accepting inputs from the wearer. For example, the buttons 280 may be configured to change the text or other information visible on the display 270. As shown in FIG. 2B, measurement platform 230 may also include one or more buttons 290 for accepting inputs from the wearer. The buttons 290 may be configured to accept inputs for controlling aspects of the data collection system, such as initiating a measurement period, or inputs indicating the wearer's current health state (i.e., normal, migraine, shortness of breath, heart attack, fever, "flu-like" symptoms, food poisoning, etc.).

Figure 3A:
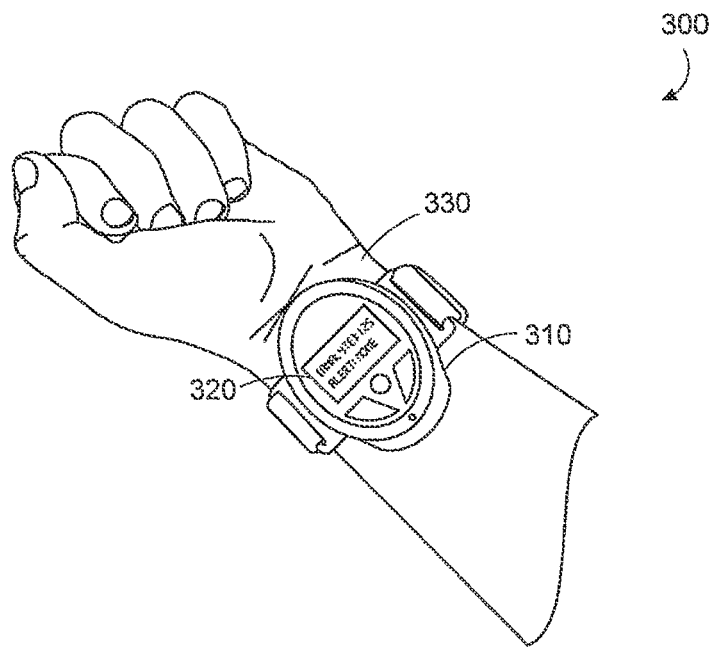
FIG. 3A is a perspective bottom view of an example wrist-mounted device, when mounted on a wearer's wrist.
Figure 3B:
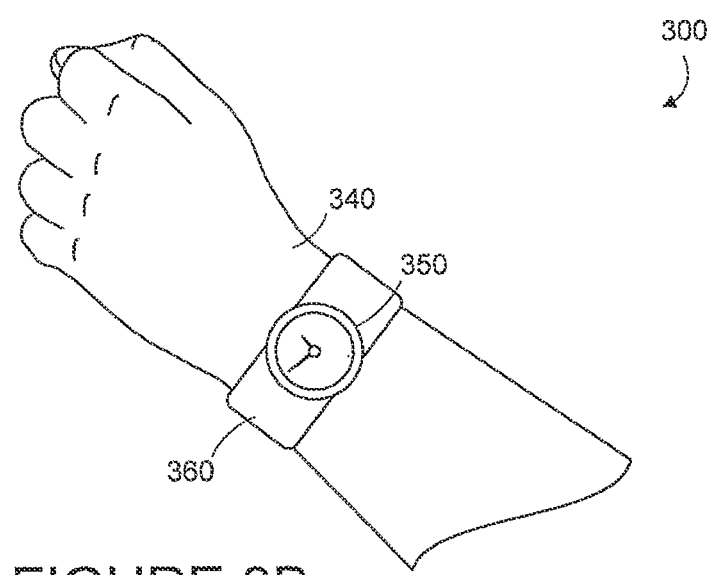
FIG. 3B is a perspective top view of an example wrist-mounted device shown in FIG. 3A, when mounted on a wearer's wrist.
Figure 3C:
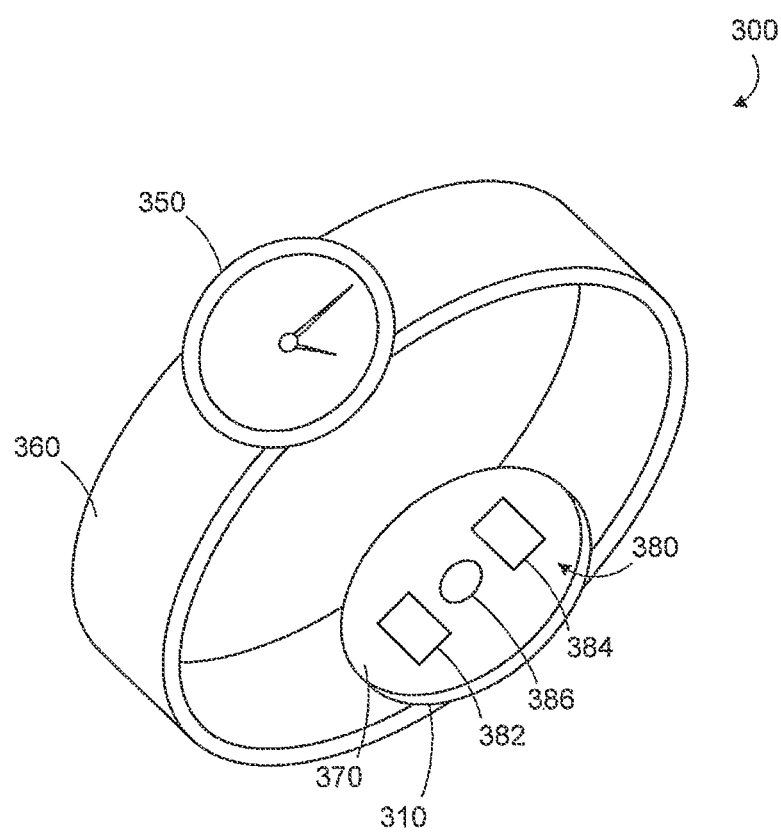
FIG. 3C is a perspective view of an example wrist-mounted device shown in FIGS. 3A and 3B.

In another example wrist-mounted device 300, shown in FIGS. 3A-3C, the measurement platform 310 and user interface 320 are both provided on the same side of the wearer's wrist, in particular, the anterior side 330 of the wrist. On the posterior side 340, a watch face 350 may be disposed on the strap 360. While an analog watch is depicted in FIG. 3B, one of ordinary skill in the art will recognize that any type of clock may be provided, such as a digital clock.

As can be seen in FIG. 3C, the inner face 370 of the measurement platform 310 is intended to be worn proximate to the wearer's body. A data collection system 380 housed on the measurement platform 310 may include a detector 382, a signal source 384 and a collection magnet 386. As described above, the signal source 384 and the collection magnet 386 may not be provided in all embodiments of the wearable device.

Figure 4A:
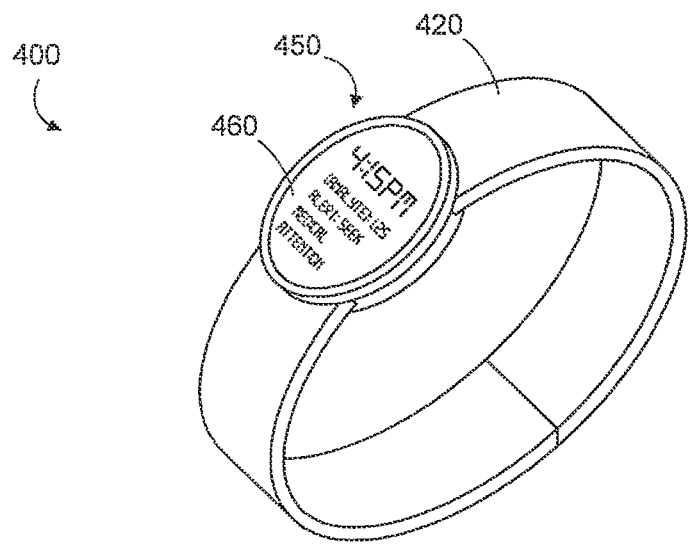
FIG. 4A is a perspective view of an example wrist-mounted device.
Figure 4B:
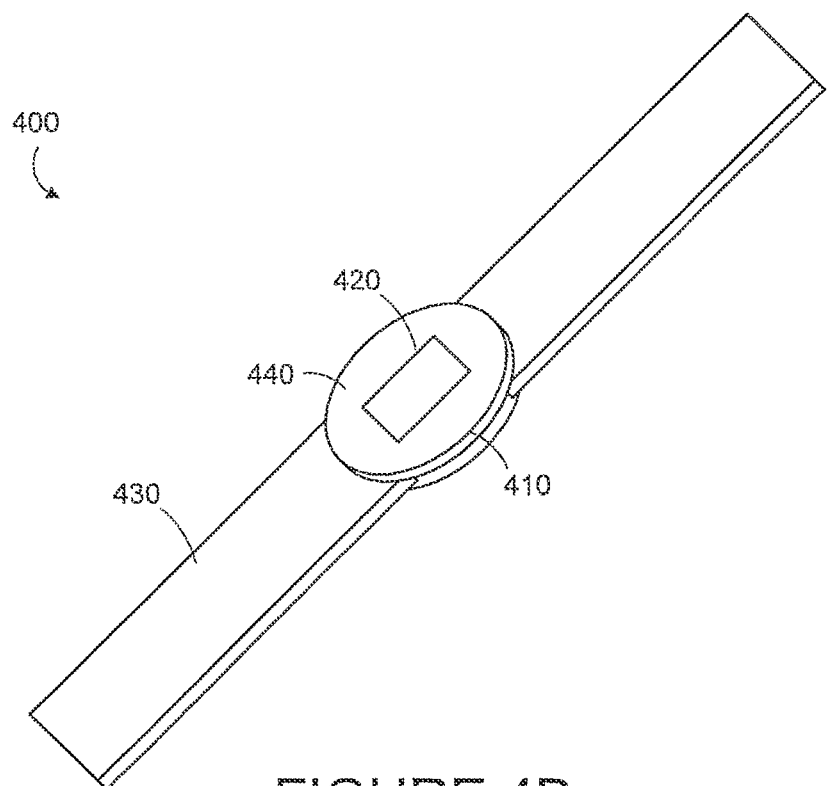
FIG. 4B is a perspective bottom view of an example wrist-mounted device shown in FIG. 4A.

In a further example shown in FIGS. 4A and 4B, a wrist mounted device 400 includes a measurement platform 410, which includes a data collection system 420, disposed on a strap 430. Inner face 440 of measurement platform may be positioned proximate to a body surface so that data collection system 420 may interrogate the subsurface vasculature of the wearer's wrist. A user interface 450 with a display 460 may be positioned facing outward from the measurement platform 410. As described above in connection with other embodiments, user interface 450 may be configured to display data collected from the data collection system 420, including the concentration of one or more measured analytes, and one or more alerts generated by a remote server or other remote computing device, or a processor located on the measurement platform. The user interface 420 may also be configured to display the time of day, date, or other information that may be relevant to the wearer.

Figure 5:
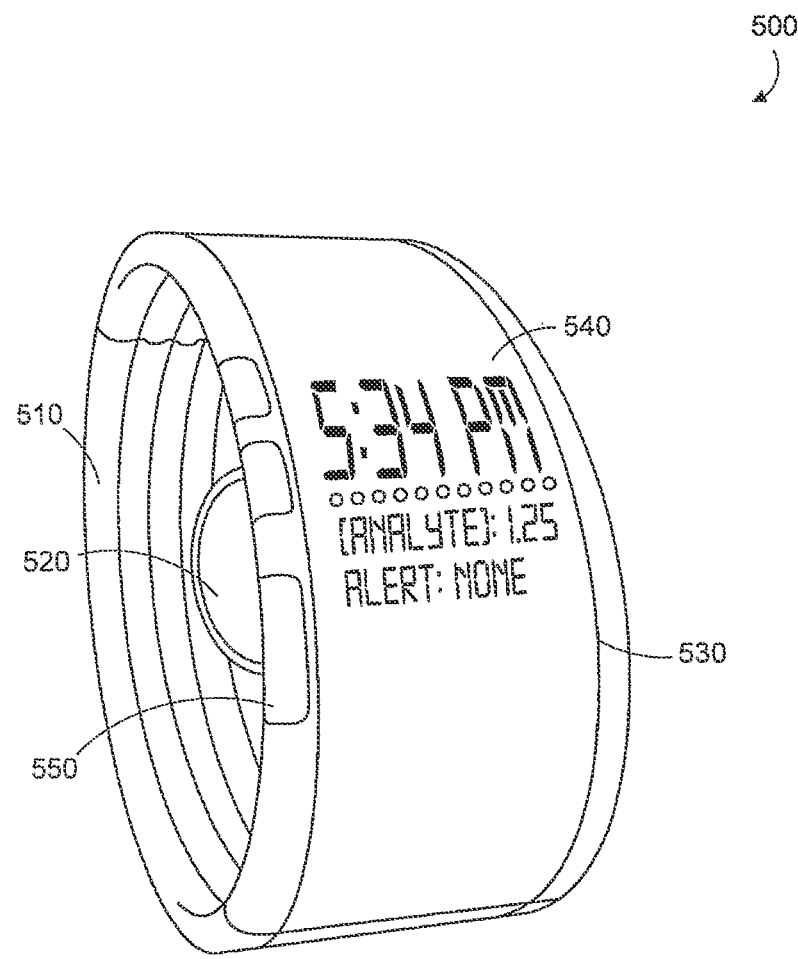
FIG. 5 is a perspective view of an example wrist-mounted device.
Figure 6:
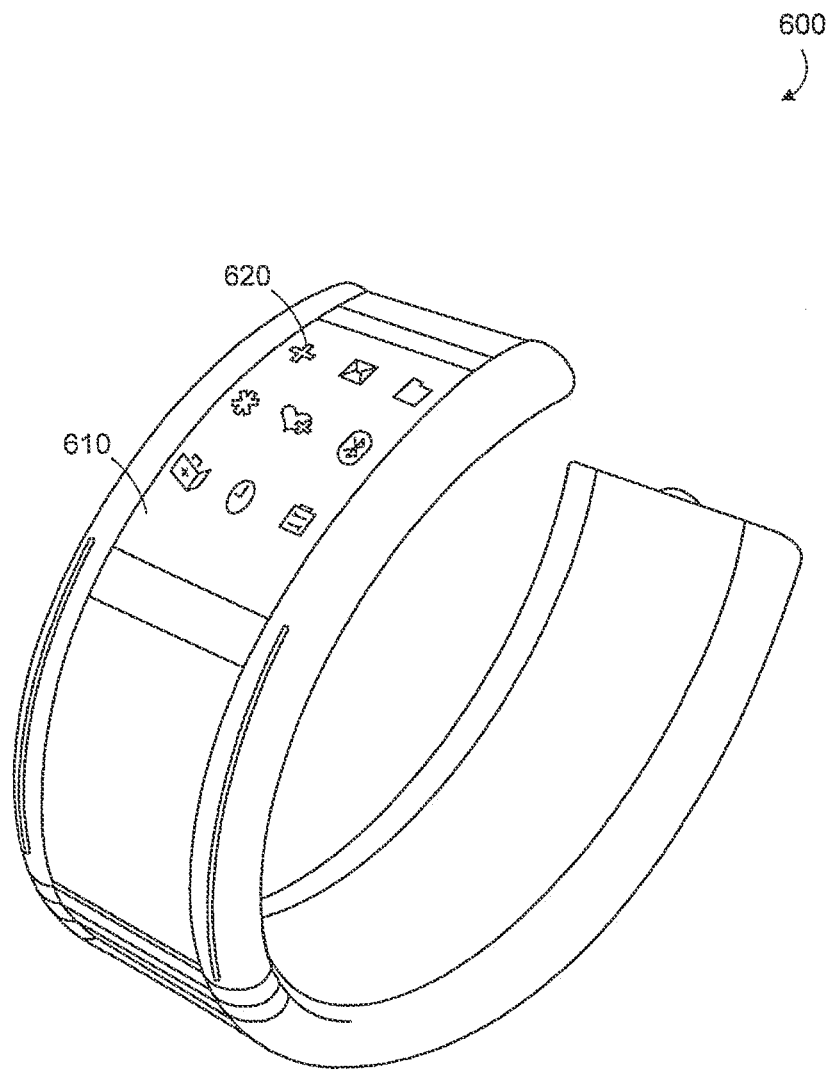
FIG. 6 is a perspective view of an example wrist-mounted device.

As shown in FIG. 5, in a further embodiment, wrist-mounted device 500 may be provided on a cuff 510. Similar to the previously discussed embodiments, device 500 includes a measurement platform 520 and a user interface 530, which may include a display 540 and one or more buttons 550. The display 540 may further be a touch-screen display configured to accept one or more input by the wearer. For example, as shown in FIG. 6, display 610 may be a touch-screen configured to display one or more virtual buttons 620 for accepting one or more inputs for controlling certain functions or aspects of the device 600, or inputs of information by the user, such as current health state.

Figure 7:
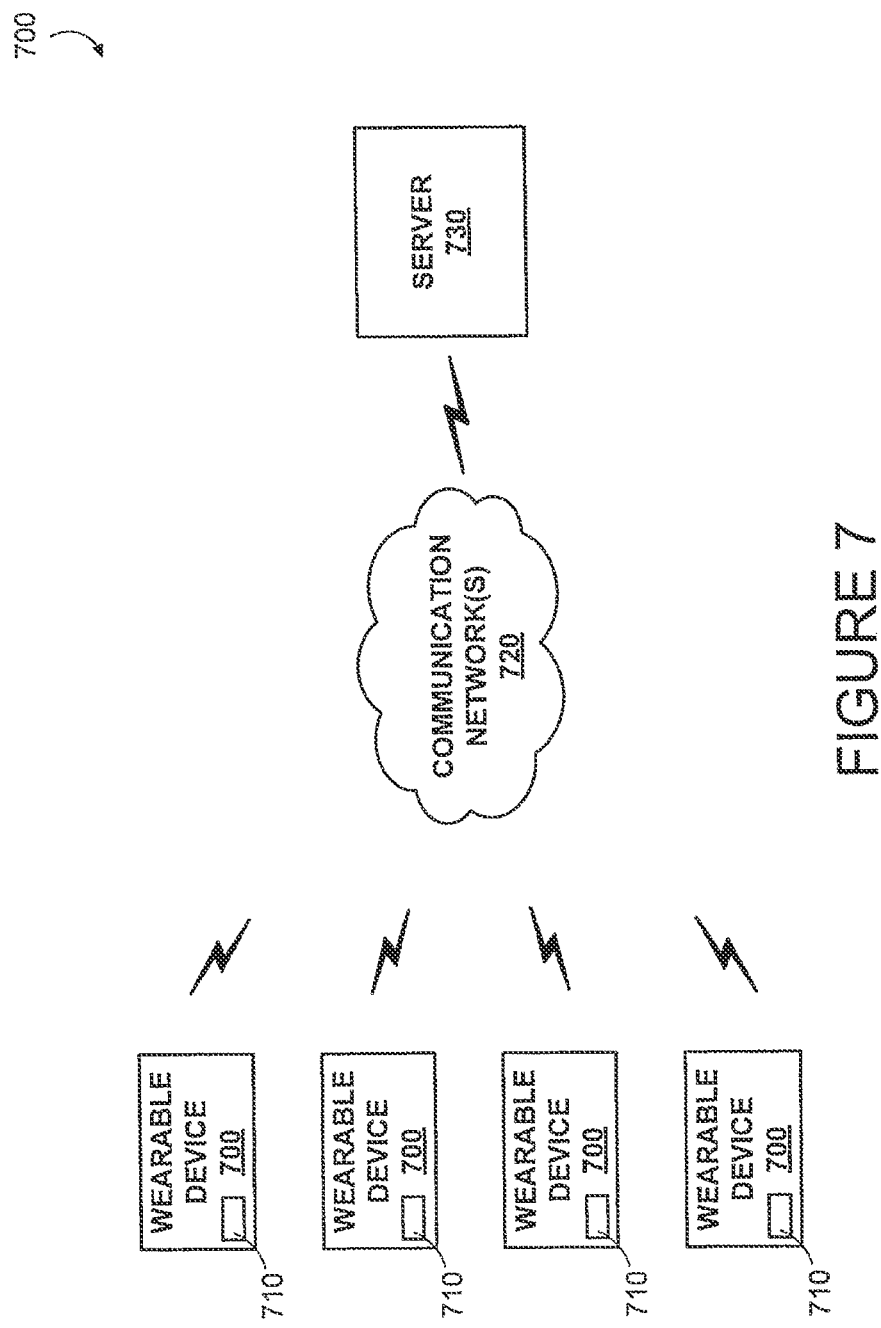
FIG. 7 is a block diagram of an example system that includes a plurality of wearable devices in communication with a server.

FIG. 7 is a simplified schematic of a system including one or more wearable devices 700. The one or more wearable devices 700 may be configured to transmit data via a communication interface 710 over one or more communication networks 720 to a remote server 730. In one embodiment, the communication interface 710 includes a wireless transceiver for sending and receiving communications to and from the server 730. In further embodiments, the communication interface 710 may include any means for the transfer of data, including both wired and wireless communications. For example, the communication interface may include a universal serial bus (USB) interface or a secure digital (SD) card interface. Communication networks 720 may be any one of may be one of: a plain old telephone service (POTS) network, a cellular network, a fiber network and a data network. The server 730 may include any type of remote computing device or remote cloud computing network. Further, communication network 720 may include one or more intermediaries, including, for example wherein the wearable device 700 transmits data to a mobile phone or other personal computing device, which in turn transmits the data to the server 730.

In addition to receiving communications from the wearable device 700, such as collected physiological parameter data and data regarding health state as input by the user, the server may also be configured to gather and/or receive either from the wearable device 700 or from some other source, information regarding a wearer's overall medical history, environmental factors and geographical data. For example, a user account may be established on the server for every wearer that contains the wearer's medical history. Moreover, in some examples, the server 730 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. Such information may be used to detect and monitor spatial and temporal spreading of diseases. As such, the wearable device may be configured to determine and/or provide an indication of its own location. For example, a wearable device may include a GPS system so that it can include GPS location information (e.g., GPS coordinates) in a communication to the server. As another example, a wearable device may use a technique that involves triangulation (e.g., between base stations in a cellular network) to determine its location. Other location-determination techniques are also possible.

The server may also be configured to make determinations regarding the efficacy of a drug or other treatment based on information regarding the drugs or other treatments received by a wearer of the device and, at least in part, the physiological parameter data and the indicated health state of the user. From this information, the server may be configured to derive an indication of the effectiveness of the drug or treatment. For example, if a drug is intended to treat nausea and the wearer of the device does not indicate that he or she is experiencing nausea after beginning a course of treatment with the drug, the server may be configured to derive an indication that the drug is effective for that wearer. In another example, a wearable device may be configured to measure blood glucose. If a wearer is prescribed a drug intended to treat diabetes, but the server receives data from the wearable device indicating that the wearer's blood glucose has been increasing over a certain number of measurement periods, the server may be configured to derive an indication that the drug is not effective for its intended purpose for this wearer.

Further, some embodiments of the system may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

Figure 8:
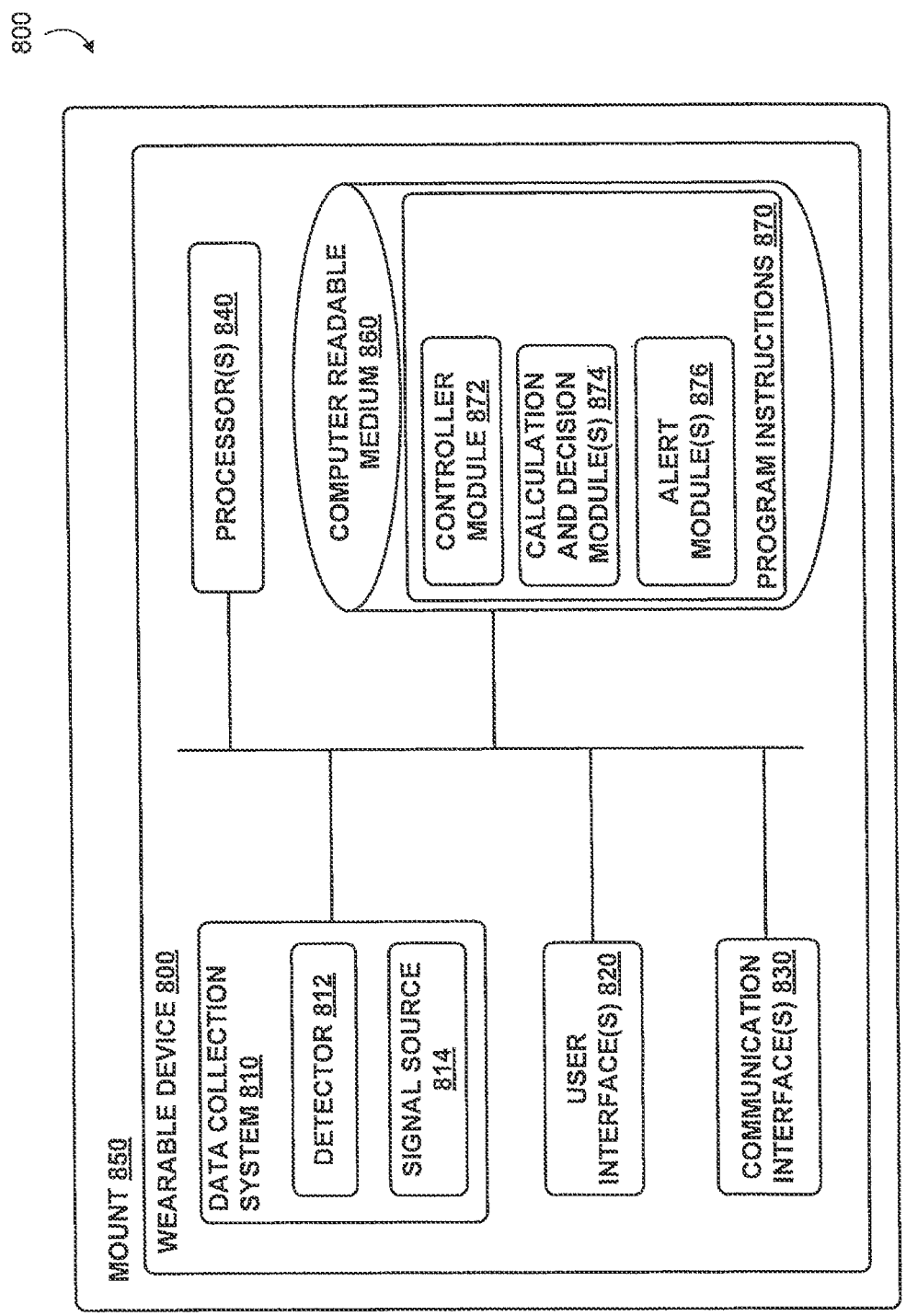
FIG. 8 is a functional block diagram of an example wearable device.

FIG. 8 is a simplified block diagram illustrating the components of a wearable device 800, according to an example embodiment. Wearable device 800 may take the form of or be similar to one of the wrist-mounted devices 200, 300, 400, 500, 600, shown in FIGS. 2A-B, 3A-3C, 4A-4C, 5 and 6. However, wearable device 800 may also take other forms, such as an ankle, waist, or chest-mounted device.

In particular, FIG. 8 shows an example of a wearable device 800 having a data collection system 810, a user interface 820, communication platform 830 for transmitting data to a server, and processor(s) 840. The components of the wearable device 800 may be disposed on a mount 850 for mounting the device to an external body surface where a portion of subsurface vasculature is readily observable.

Processor 840 may be a general-purpose processor or a special purpose processor (e.g., digital signal processors, application specific integrated circuits, etc.). The one or more processors 840 can be configured to execute computer-readable program instructions 870 that are stored in the computer readable medium 860 and are executable to provide the functionality of a wearable device 800 described herein.

The computer readable medium 860 may include or take the form of one or more non-transitory, computer-readable storage media that can be read or accessed by at least one processor 840. The one or more computer-readable storage media can include volatile and/or non-volatile storage components, such as optical, magnetic, organic or other memory or disc storage, which can be integrated in whole or in part with at least one of the one or more processors 840. In some embodiments, the computer readable medium 860 can be implemented using a single physical device (e.g., one optical, magnetic, organic or other memory or disc storage unit), while in other embodiments, the computer readable medium 860 can be implemented using two or more physical devices.

Data collection system 810 includes a detector 812 and, in some embodiments, a signal source 814. As described above, detector 812 may include any detector capable of detecting at least one physiological parameter, which could include any parameters that may relate to the health of the person wearing the wearable device. For example, the detector 812 could be configured to measure blood pressure, pulse rate, skin temperature, etc. At least one of the detectors 812 is configured to non-invasively measure one or more analytes in blood circulating in subsurface vasculature proximate to the wearable device. In some examples, detector 812 may include one or more of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor.

In some examples, the data collection system 810 further includes a signal source 814 for transmitting an interrogating signal that can penetrate the wearer's skin into the portion of subsurface vasculature. In general, signal source 814 will generate an interrogation signal that will produce a responsive signal that can be detected by one or more of the detectors 812. The interrogating signal can be any kind of signal that is benign to the wearer, such as electromagnetic, magnetic, optic, acoustic, thermal, mechanical, and results in a response signal that can be used to measure a physiological parameter or, more particularly, that can detect the binding of the clinically-relevant analyte to the functionalized particles. In one example, the interrogating signal is an electromagnetic pulse (e.g., a radio frequency (RF) pulse) and the response signal is a magnetic resonance signal, such as nuclear magnetic resonance (NMR). In another example, the interrogating signal is a time-varying magnetic field, and the response signal is an externally-detectable physical motion due to the time-varying magnetic field. The time-varying magnetic field modulates the particles by physical motion in a manner different from the background, making them easier to detect. In a further example, the interrogating signal is an electromagnetic radiation signal. In particular, the interrogating signal may be electromagnetic radiation having a wavelength between about 400 nanometers and about 1600 nanometers. The interrogating signal may, more particularly, comprise electromagnetic radiation having a wavelength between about 500 nanometers and about 1000 nanometers. In examples where the functionalized particles include a fluorophore, the interrogating signal may therefore be an electromagnetic radiation signal with a wavelength that can excite the fluorophore and penetrate the skin or other tissue and subsurface vasculature (e.g., a wavelength in the range of about 500 to about 1000 nanometers), and the response signal is fluorescence radiation from the fluorophore that can penetrate the subsurface vasculature and tissue to reach the detector.

The program instructions 870 stored on the computer readable medium 860 may include instructions to perform or facilitate some or all of the device functionality described herein. For instance, in the illustrated embodiment, program instructions 870 include a controller module 872, calculation and decision module 874 and an alert module 876.

The controller module 872 can include instructions for operating the data collection system 810, for example, the detector 812 and signal source 814. For example, the controller 872 may activate signal source 814 and/or detector 812 during each of the pre-set measurement periods. In particular, the controller module 872 can include instructions for controlling the signal source 814 to transmit an interrogating signal at preset measurement times and controlling the detector 812 to receive data representative of response signals transmitted from the portion of subsurface vasculature in response to the interrogating signals transmitted at the preset measurement times.

The controller module 872 can also include instructions for operating a user interface 820. For example, controller module 872 may include instructions for displaying data collected by the data collection system 810 and analyzed by the calculation and decision module 874, or for displaying one or more alerts generated by the alert module 875. Further, controller module 872 may include instructions to execute certain functions based on inputs accepted by the user interface 820, such as inputs accepted by one or more buttons disposed on the user interface.

Communication platform 830 may also be operated by instructions within the controller module 872, such as instructions for sending and/or receiving information via a wireless antenna, which may be disposed on or in the wearable device 800. The communication interface 830 can optionally include one or more oscillators, mixers, frequency injectors, etc. to modulate and/or demodulate information on a carrier frequency to be transmitted and/or received by the antenna. In some examples, the wearable device 800 is configured to indicate an output from the processor by modulating an impedance of the antenna in a manner that is perceivable by a remote server or other remote computing device.

Calculation and decision module 872 may include instructions for receiving data from the data collection system 810 in the form of a responsive signal, analyzing the data to determine if the target analyte is present or absent, quantify the measured physiological parameter(s), such as concentration of a target analyte, and analyzing the data to determine if a medical condition is indicated. In particular, the calculation and decision module 872 may include instructions for determining, for each preset measurement time, a concentration of a clinically-relevant analyte based on the response signal detected by the detector at that measurement time and determining, for each preset measurement time, whether a medical condition is indicated based on at least the corresponding concentration of the clinically-relevant analyte. The preset measurement times may be set to any period and, in one example, are about one hour apart.

The program instructions of the calculation and decision module 872 may, in some examples, be stored in a computer-readable medium and executed by a processor located external to the wearable device. For example, the wearable device could be configured to collect certain data regarding physiological parameters from the wearer and then transmit the data to a remote server, which may include a mobile device, a personal computer, the cloud, or any other remote system, for further processing.

The computer readable medium 860 may further contain other data or information, such as medical and health history of the wearer of the device, that may be necessary in determining whether a medical condition is indicated. Further, the computer readable medium 860 may contain data corresponding to certain analyte baselines, above or below which a medical condition is indicated. The baselines may be pre-stored on the computer readable medium 860, may be transmitted from a remote source, such as a remote server, or may be generated by the calculation and decision module 874 itself. The calculation and decision module 874 may include instructions for generating individual baselines for the wearer of the device based on data collected over a certain number of measurement periods. For example, the calculation and decision module 874 may generate a baseline concentration of a target blood analyte for each of a plurality of measurement periods by averaging the analyte concentration at each of the measurement periods measured over the course of a few days, and store those baseline concentrations in the computer readable medium 860 for later comparison. Baselines may also be generated by a remote server and transmitted to the wearable device 800 via communication interface 830. The calculation and decision module 874 may also, upon determining that a medical condition is indicated, generate one or more recommendations for the wearer of the device based, at least in part, on consultation of a clinical protocol. Such recommendations may alternatively be generated by the remote server and transmitted to the wearable device.

In some examples, the collected physiological parameter data, baseline profiles, health state information input by device wearers and generated recommendations and clinical protocols may additionally be input to a cloud network and be made available for download by a wearer's physician. Trend and other analyses may also be performed on the collected data, such as physiological parameter data and health state information, in the cloud computing network and be made available for download by physicians or clinicians.

Further, physiological parameter and health state data from individuals or populations of device wearers may be used by physicians or clinicians in monitoring efficacy of a drug or other treatment. For example, high-density, real-time data may be collected from a population of device wearers who are participating in a clinical study to assess the safety and efficacy of a developmental drug or therapy. Such data may also be used on an individual level to assess a particular wearer's response to a drug or therapy. Based on this data, a physician or clinician may be able to tailor a drug treatment to suit an individual's needs.

In response to a determination by the calculation and decision module 874 that a medical condition is indicated, the alert module 876 may generate an alert via the user interface 820. The alert may include a visual component, such as textual or graphical information displayed on a display, an auditory component (e.g., an alarm sound), and/or tactile component (e.g., a vibration). The textual information may include one or more recommendations, such as a recommendation that the wearer of the device contact a medical professional, seek immediate medical attention, or administer a medication.

Figure 9A:
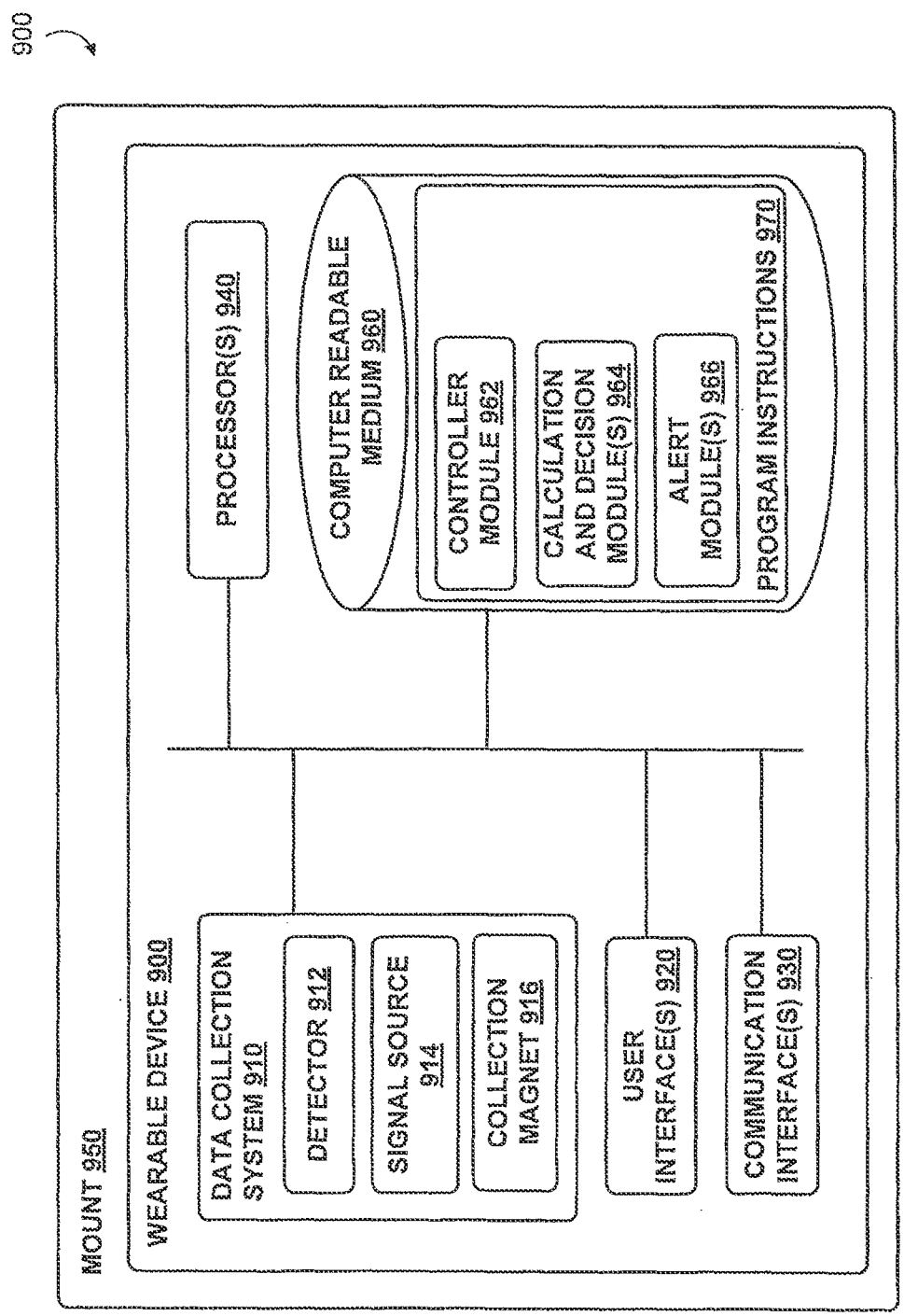
FIG. 9A is a functional block diagram of an example wearable device.

FIG. 9A is a simplified block diagram illustrating the components of a wearable device 900, according to an example embodiment. Wearable device 900 is similar to wearable device 800, except that the data collection system 910 of wearable device 900 further includes a collection magnet 916. In this example, the collection magnet 916 may be used to locally collect functionalized magnetic particles present in an area of subsurface vasculature proximate to the collection magnet 916. As described above, collection magnet 916 is configured to direct a magnetic field into a portion of subsurface vasculature sufficient to cause functionalized magnetic particles to collect in a lumen of the portion of subsurface vasculature.

Wearable device 900 includes a data collection system 910, which includes a detector 912, a signal source 914 (if provided) and a collection magnet 916, a user interface 920, a communication interface 930, a processor 940 and a computer readable medium 960 on which program instructions 970 are stored. All of the components of wearable device 900 may be provided on a mount 950. In this example, the program instructions 970 may include a controller module 962, a calculation and decision module 964 and an alert module 966 which, similar to the example set forth in FIG. 8, include instructions to perform or facilitate some or all of the device functionality described herein. Controller module 962 further includes instructions for operating collection magnet 916. For example, controller module 962 may include instructions for activating collection magnet during a measurement period, for a certain amount of time.

Figure 9B:
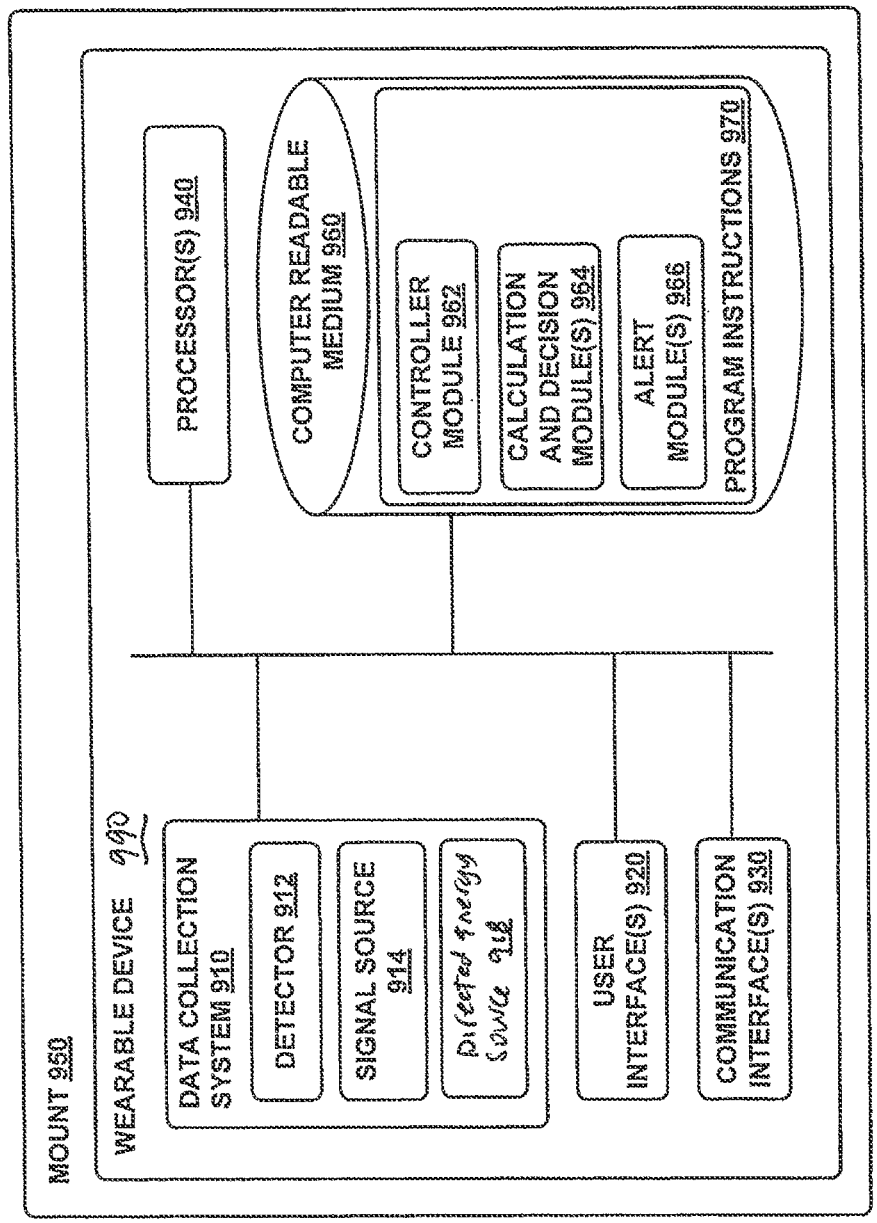
FIG. 9B is a functional block diagram of an example wearable device.

FIG. 9B is a simplified block diagram illustrating the components of another wearable device 990, according to an example embodiment. Wearable device 990 is similar to the wearable device 900 shown in FIG. 9A, except that the data collection system 910 of wearable device 900 further includes a directed energy source 918. Wearable device 990 may also include collection magnet 916 (not shown). In this example, the directed energy source 918 is configured to direct energy such as electromagnetic radiation, acoustic energy or heat to tissue from an external surface to trigger the release of a biologically active agent from an inactive state to an active state in order to treat a medical condition or to maintain a health state.

As shown in FIGS. 9A and 9B, the program instructions 970 may include a controller module 962, a calculation and decision module 964 and an alert module 966 which, similar to the example set forth in FIG. 8, include instructions to perform or facilitate some or all of the device functionality described herein. Based on the determined concentration or abundance of the target analyte, processor 940 may be further configured to control the rate of conversion of the biologically active agent to the active state, to assess the effect of the biologically active agent on the state of the living body, and/or to trigger the source 918 to apply the directed energy. Controller module 962 may also further include instructions for operating the source of directed energy 918. For example, controller module 962 may include instructions for activating the directed energy source to generate a pulse or a series of pulses or cycle of pulses for a certain amount of time.

FIG. 9C is a simplified block diagram illustrating the components of an example system 1800, including a wearable device 1810. Wearable device 1810 may take the form of or be similar to one of the wrist-mounted devices 200, 300, 400, 500, or 600 shown in FIGS. 2A-B, 3A-3C, 4A-4C, 5, and 6. However, wearable device 1810 may also take other forms, such as an ankle, waist, ear, eye or chest-mounted device. Further, any of devices 200, 300, 400, 500, and 600 may be configured similar to or include any of the components of system 1800, including wearable device 1810.

In particular, FIG. 9C shows an example of a system 1800 including a wearable device 1810 having a detector 1812, in some examples, a signal source 1814, a modulation source 1816, a directed energy source 1818, and a communication interface 1820, controlled by a controller 1830. Communication interface 1820 may include an antenna. The components of the wearable device 1810 may be disposed on a mount (not shown) for mounting the device to an external body surface where a portion of subsurface vasculature is readily observable. System 1800 may further include a remote device 1840 in communication with the wearable device 1810, including a processor 1850, a computer readable medium 1860, a user interface 1870, and a communication interface 1880 for communicating with the wearable device 1810 and/or for transmitting data to a server or other remote computing device. While FIG. 9C depicts various components of system 1800 disposed on the wearable device 1810 or the remote device 1840, one of ordinary skill in the art would understand that different configurations and designs are possible, including where all of the components are provided on the wearable device.

Processor 1850 may be a general-purpose processor or a special purpose processor (e.g., digital signal processors, application specific integrated circuits, etc.) and can be configured to execute computer-readable program instructions 1862 that are stored in the computer readable medium 1860 and are executable to provide the functionality of a system 1800 as described herein. The computer readable medium 1850 may include or take the form of one or more non-transitory, computer-readable storage media that can be read or accessed by the processor 1850, and can include volatile and/or non-volatile storage components, such as optical, magnetic, organic or other memory or disc storage, which can be integrated in whole or in part with the processor 1850. The controller 1830 may be configured to operate one or more of the detector 1812, signal source 1814, modulation source 1816, and directed energy source 1818. For example, the controller 1830 may activate the detector 1812, signal source 1814 and modulation source 1816 during each of the pre-set measurement periods.

The program instructions 1862 stored on the computer readable medium 1860 may include instructions to perform or facilitate some or all of the system functionality described herein. For instance, in the illustrated embodiment, program instructions 1862 may include instructions for controller 1830 to operate the detector 1812, signal source 1814, modulation source 1816, and directed energy source 1818.

Program instructions 1862 may further cause the processor 1850 to detect the one or more target analytes by differentiating the analyte response signal from the background signal based, at least in part, on a modulation applied by the modulation source 1816. In some cases, the processor may further be configured to differentiate the analyte response signal from the unbound particle signal. Further, the processor 1850 may be configured to determine the concentration of a particular target analyte in the blood from, at least in part, the analyte response signal. The detection and concentration data processed by the processor may be communicated to the patient, for example via the user interface 1870, transmitted to medical or clinical personnel, locally stored or transmitted to a remote server, the cloud, and/or any other system where the data may be stored or accessed at a later time. The program instructions 1862 may also include instructions for operating a user interface 1870, for example, instructions for displaying data transmitted from the wearable device 1810 and analyzed by the processor 1850, or for generating one or more alerts. Furthermore, the programing instructions 1862 may, based on the determination of the presence or absence of one or more target analytes, concentration or abundance of the one or more analytes, and other physiological parameters, direct the processor 1850 to reactivate the directed energy source 1818 to apply an additional pulse, a series of pulses or multiple cycles of pulses to further convert additional biologically active agent to an active state from an inactive state.

IV. ILLUSTRATIVE FUNCTIONALIZED PARTICLES

In some examples, the wearable devices described above obtain at least some of the health-related information by detecting the binding of a clinically-relevant analyte to functionalized particles, for example, microparticles or nanoparticles. The particles can be functionalized by covalently attaching a bioreceptor designed to selectively bind or otherwise recognize a particular clinically-relevant analyte. For example, particles may be functionalized with a variety of bioreceptors, including antibodies, nucleic acids (DNA, siRNA), low molecular weight ligands (folic acid, thiamine, dimercaptosuccinic acid), peptides (RGD, LHRD, antigenic peptides, internalization peptides), proteins (BSA, transferrin, antibodies, lectins, cytokines, fibrinogen, thrombin), polysaccharides (hyaluronic acid, chitosan, dextran, oligosaccharides, heparin), polyunsaturated fatty acids (palmitic acid, phospholipids), plasmids. The functionalized particles can be introduced into the person's blood stream by injection, ingestion, inhalation, transdermally, or in some other manner.

The clinically-relevant analyte could be any analyte that, when present in or absent from the blood, or present at a particular concentration or range of concentrations, may be indicative of a medical condition or indicative that a medical condition may be imminent. For example, the clinically-relevant analyte could be an enzyme, hormone, protein, or other molecule. In one relevant example, certain protein biomarkers are known to be predictive of an impending arterial plaque rupture. Such protein biomarkers are known to be present in the blood only directly leading up to and at the onset of an arterial plaque rupture. Plaques that rupture cause the formation of blood clots that can block blood flow or break off and travel to another part of the body. In either of these cases, if a clot blocks a blood vessel that feeds the heart, it causes a heart attack. If it blocks a blood vessel that feeds the brain, it causes a stroke. If blood supply to the arms or legs is reduced or blocked, it can cause difficulty walking and eventually gangrene. The presence of these protein biomarkers in the vasculature may be detected, and the medical condition (i.e., stroke, heart attack) prevented, by providing particles functionalized with a bioreceptor that will selectively bind to this target analyte.

The particles may be made of biodegradable or non-biodegradable materials. For example, the particles may be made of polystyrene. Non-biodegradable particles may be provided with a removal means to prevent harmful buildup in the body. Generally, the particles may be designed to have a long half-life so that they remain in the vasculature or body fluids over several measurement periods. Depending on the lifetime of the particles, however, the user of the wearable device may periodically introduce new batches of functionalized particles into the vasculature or body fluids.

Bioreceptors can be used in diagnostic procedures, or even in therapy to destroy a specific target, such as antitumor therapy or targeted chemotherapy. The particles may be designed to remove from the body or destroy the target analyte once bound to the bioreceptor. Additional functional groups may be added to the particles to signal that the particles can be removed from the body through the kidneys, for example, once bound to the target analyte.

Further, the particles may be designed to either releasably or irreversibly bind to the target analyte. For example, if it is desired for the particles to participate in destruction or removal of the target analyte from the body, as described above, the particles may be designed to irreversibly bind to the target analyte. In other examples, the particles may be designed to release the target analyte after measurement has been made, either automatically or in response to an external or internal stimulus.

Those of skill in the art will understand the term "particle" in its broadest sense and that it may take the form of any fabricated material, a molecule, cryptophan, a virus, a phage, etc. Further, a particle may be of any shape, for example, spheres, rods, non-symmetrical shapes, etc., and may be made of a solid, liquid or gaseous material or combinations thereof. The particles can have a diameter that is less than about 20 micrometers. In some embodiments, the particles have a diameter on the order of about 10 nanometers to 1 micrometer. In further embodiments, small particles on the order of 10-100 nanometers in diameter may be assembled to form a larger "clusters" or "assemblies on the order of 1-10 micrometers. In this arrangement, the assemblies would provide the signal strength of a larger particle, but would be deformable, thereby preventing blockages in smaller vessels and capillaries.

Binding of the functionalized particles to a target analyte may be detected with or without a stimulating signal input. The term "binding" is understood in its broadest sense to include any detectable interaction between the receptor and the target analyte. For example, some particles may be functionalized with compounds or molecules, such as fluorophores or autofluorescent, luminescent or chemiluminescent markers, which generate a responsive signal when the particles bind to the target analyte without the input of a stimulus. In other examples, the functionalized particles may produce a different responsive signal in their bound versus unbound state in response to an external stimulus, such as an electromagnetic, acoustic, optical, or mechanical energy.

Further, the particles may be formed from a paramagnetic or ferromagnetic material or be functionalized with a magnetic moiety. The magnetic properties of the particles can be exploited in magnetic resonance detection schemes to enhance detection sensitivity. In another example, an external magnet may be used to locally collect the particles in an area of subsurface vasculature during a measurement period. Such collection may not only increase the differential velocity between particles and analytes, hence surveying a much larger volume per unit time, but may also enhance the signal for subsequent detection.

V. ILLUSTRATIVE METHODS FOR OPERATION OF A WEARABLE DEVICE

Figure 10:
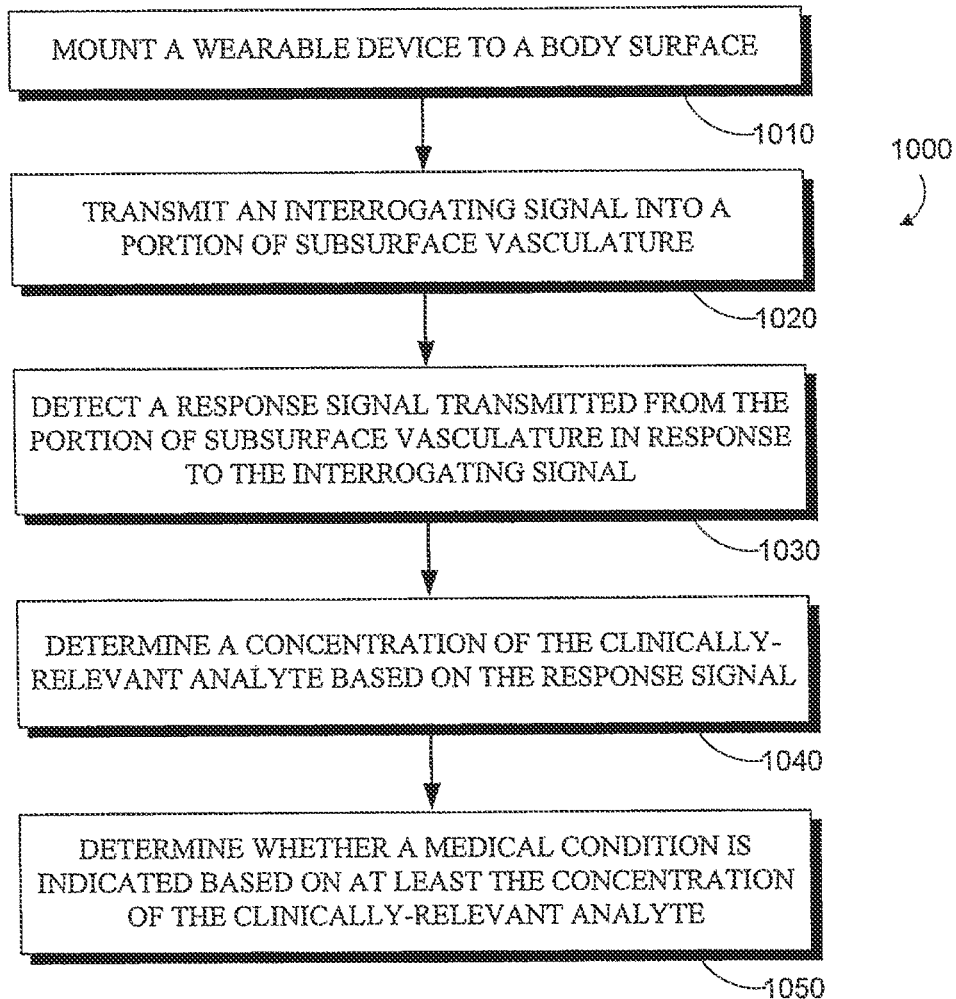
FIG. 10 is a flowchart of an example method for operating a wearable device.

FIG. 10 is a flowchart of a method 1000 for operating a wearable device to take non-invasive, in vivo, real-time measurements of physiological parameters. A wearable device is first mounted to a body surface of a human subject, wherein the body surface is proximate to a portion of subsurface vasculature (1010). In some examples, the wearable device, via a signal source, transmits an interrogating signal into the portion of subsurface vasculature (1020). The wearable device, via a detector, then detects a response signal transmitted from the portion of subsurface vasculature, wherein the response signal is related to binding of a clinically-relevant analyte to functionalized particles present in a lumen of the subsurface vasculature (1030). In some examples, the response signal is generated in response to an interrogating signal. The functionalized particles are configured to bind to the clinically-relevant analyte and may comprise a receptor, such as an antibody. The term "bind" is understood in its broadest sense to also include any detectable interaction between the clinically relevant analyte and the functionalized particles. The wearable device then determines the presence, absence and/or a concentration of the clinically-relevant analyte based on the response signal (1040) and whether a medical condition is indicated based on at least the presence, absence and/or concentration of the clinically-relevant analyte (1040). Further, in examples where the functionalized particles are magnetic, the wearable device may further direct a magnetic field into the portion of subsurface vasculature, the magnetic field being sufficient to cause the functionalized magnetic particles to collect in a lumen of the portion of subsurface vasculature.

FIGS. 11A-11B, 12A-12B, and 13A-13B are partial cross-sectional side views of a human wrist illustrating the operation of various examples of a wrist-mounted device. In the example shown in FIGS. 11A and 11B, the wrist-mounted device 1100 includes a measurement platform 1110 mounted on a strap or wrist-band 1120 and oriented on the anterior side 1190 of the wearer's wrist. Measurement platform 1110 is positioned over a portion of the wrist where subsurface vasculature 1130 is easily observable. Functionalized particles 1140 have been introduced into a lumen of the subsurface vasculature by one of the means discussed above. In this example, measurement platform 1110 includes a data collection system having both a detector 1150 and a signal source 1160. FIG. 11A illustrates the state of the subsurface vasculature when measurement device 1100 is inactive. The state of the subsurface vasculature during a measurement period is illustrated in FIG. 11B. At this time, signal source 1160 is transmitting an interrogating signal 1162 into the portion of subsurface vasculature and detector 1150 is receiving a response signal 1152 generated in response to the interrogating signal 1162. The response signal 1152 is related to the binding of a clinically relevant analyte present in the subsurface vasculature to the functionalized particles 1140. As described above, in some embodiments, an interrogating signal may not be necessary to generate a response signal related to the binding of an analyte to the functionalized particles.

Figure 12A:
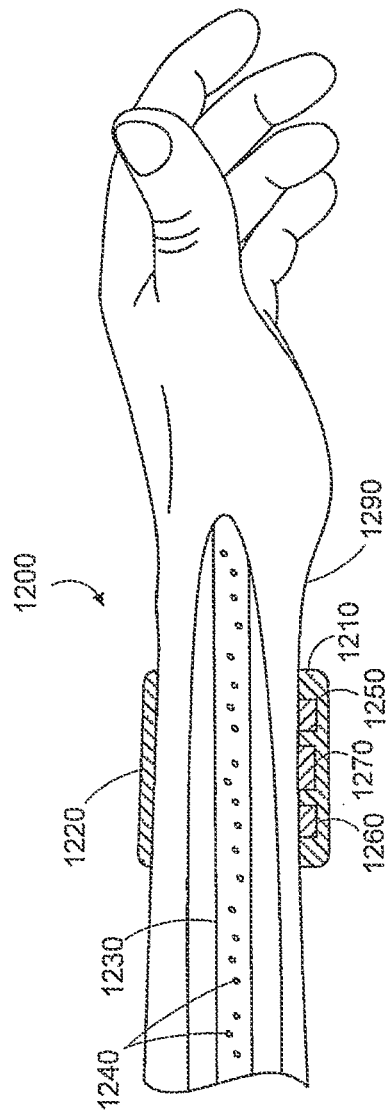
FIG. 12A is side partial cross-sectional view of a wrist-mounted device, while on a human wrist.
Figure 12B:
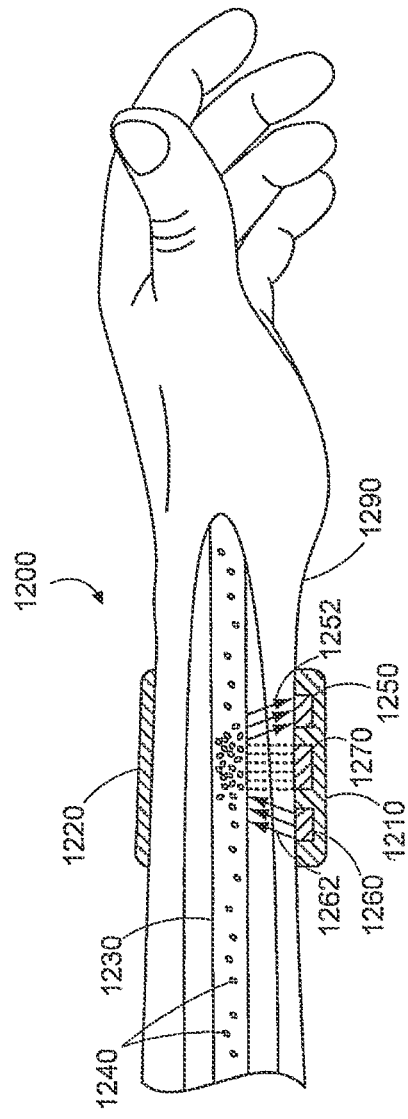
FIG. 12B is side partial cross-sectional view of a wrist-mounted device, while on a human wrist.

Similar to the system depicted in FIGS. 11A and 11B, FIGS. 12A and 12B illustrate a wrist-mounted device 1200 including a measurement platform 1210 mounted on a strap or wristband 1220 and oriented on the anterior side 1290 of the wearer's wrist. In this example, measurement platform 1210 includes a data collection system having a detector 1250, a signal source 1260 and a collection magnet 1270. FIG. 12A illustrates the state of the subsurface vasculature when measurement device 1200 is inactive. The state of the subsurface vasculature when measurement device 1200 is active during a measurement period is illustrated in FIG. 12B. At this time, collection magnet 1270 generates a magnetic field 1272 sufficient to cause functionalized magnetic particles 1240 present in a lumen of the subsurface vasculature 1230 to collection in a region proximal to the magnet 1270. Signal source 1260 transmits an interrogating signal 1262 into the portion of subsurface vasculature and detector 1250 is receiving a response signal 1252 generated in response to the interrogating signal 1262. The response signal 1252 is related to the binding of a clinically relevant analyte present in the subsurface vasculature to the functionalized magnetic particles 1240. As described above, in some embodiments, an interrogating signal may not be necessary to generate a response signal related to the binding of an analyte to the functionalized magnetic particles.

FIGS. 13A and 13B illustrate a further embodiment of a wrist-mounted device 1300 having a measurement platform 1310 disposed on a strap 1320, wherein the detector 1350 and signal source 1360 are positioned on the posterior side 1390 of the wearer's wrist and the collection magnet 1370 is disposed on the anterior side 1380 of the wearer's wrist. Similar to the embodiments discussed above, FIG. 13A illustrates the state of the subsurface vasculature when measurement device 1300 is inactive. The state of the subsurface vasculature when measurement device 1300 is active during a measurement period is illustrated in FIG. 13B. At this time, collection magnet 1370 generates a magnetic field 1232 sufficient to cause functionalized magnetic particles 1340 present in a lumen of the subsurface vasculature 1330 to collection in a region proximal to the magnet 1370. Signal source 1360 transmits an interrogating signal 1362 into the portion of subsurface vasculature and detector 1350 is receiving a response signal 1352 generated in response to the interrogating signal 1262. The response signal 1352 is related to the binding of a clinically relevant analyte present in the subsurface vasculature to the functionalized magnetic particles 1340. As described above, in some embodiments, an interrogating signal may not be necessary to generate a response signal related to the binding of an analyte to the functionalized magnetic particles.

Both FIGS. 12B and 13B illustrate the path of the interrogating signal (1262, 1362) transmitted by the signal source (1260, 1360) and the responsive signal (1252, 1352) detected by the detector (1250, 1350) essentially overlapping over a portion of subsurface vasculature. In some examples, the signal source (1260, 1360) and the detector (1250, 1350) may be angled towards each other so that they are interrogating and detecting from essentially the same area of subsurface vasculature. However, in some instances, such as in the example shown in FIG. 11B, the paths of the interrogating signal (1262, 1362) transmitted by the signal source (1260, 1360) and the responsive signal (1252, 1352) detected by the detector (1250, 1350) may not overlap.

VI. ILLUSTRATIVE METHODS FOR REAL-TIME, HIGH-DENSITY PHYSIOLOGICAL DATA COLLECTION USING A WRIST MOUNTED DEVICE

In a representative example, after a baseline profile of a patient is obtained, a patient receives an infusion of a bioactive agent (e.g., anti-tumor agent) encapsulated in gold nanoparticle carriers. A source of directed energy, for instance, radiofrequency transmitter device that directs a radiofrequency signal of sufficient power to rapidly heat and rupture the gold nanoparticle encapsulates (but at levels that is benign to the patient), is then applied to the patient at a desired rate by medical personnel. The status of the patient can be monitored prior to, during, or after receiving treatment.

FIG. 14 is a flowchart of a method 1400 for using a wearable device to take real-time, high-density, non-invasive, in vivo measurements of physiological parameters. In a first step, the wearable device automatically measures one or more physiological parameters during each of a plurality of measurement periods (1410). The length of the measurement period may be set on the device itself or may be set remotely, for example, by instruction from a remote server. The device may be configured with many measurement periods each day—for example, continuous, every second, every minute, every hour, every 6 hours, etc.—or may be configured to take measurements once a week or once a month. Further, a different measurement period may be set for each of the physiological parameters being measured. The measurement periods may extend through a plurality of consecutive days and each of the consecutive days may include multiple measurement periods. Each of the consecutive days may further include at least twenty-four measurement periods and the plurality of consecutive days may include at least thirty days. At least some of the physiological parameters are measured by non-invasively detecting one or more analytes in blood circulating in subsurface vasculature proximate to the wearable device.

After conclusion of a measurement period, for each of the plurality of measurement periods, the wearable device transmits to a server data representative of the physiological parameters measured during that measurement period (1420). The wearable device may be configured to automatically transmit the data to a server, may be configured to transmit on command of the wearer, or may be configured to transmit on instruction from a remote server. Further, the device may be configured to automatically transmit the data at the end of each measurement period, or at some more frequent or infrequent rate. For example, the device could be configured to transmit every five minutes, at the end of each day, at the end of the month, at nighttime only, etc.

In response, the server is configured to develop a baseline profile based on the data transmitted by the wearable device for the plurality of measurement periods (1430). In some embodiments, the baseline profile includes an individual baseline profile based on the data transmitted by the wearable device for the plurality of measurement periods for an individual user wearing the wearable device. As described above, the baseline profile may include patterns for how one or more of the wearer's physiological parameters typically change over time, such as during the course of a day, a week, or a month. The baseline profile may further include threshold values of certain target analytes, above or below which a medical condition may be indicated.

After the server has developed an individual baseline profile for a wearer of the device, the biologically active agent in an inactive state may be administered (1435) to the wearer by any suitable means including ingestion, injection or infusion. Directed energy is then applied to the tissue from an external surface of the wearer's body to convert the biologically active agent from the inactive state to the active state (1435). The server may receive additional data regarding the physiological parameters from the wearable device measured during one or more additional measurement periods (1440) during and after administration and activation of the biologically active agent. The server may then compare the additional data, collected over additional measurement periods, to the individual baseline profile. If the additional data is consistent with the patterns embodied in the individual baseline profile, the server may determine that the wearer's condition has not changed. On the other hand, if the additional data deviates from the patterns embodied in the baseline profile, the server may detect a change in the wearer's condition (1450). The changes in the wearer's condition as determined, for instance, by changes in the presence or absence of one or more target analytes or changes in the concentrations or abundance of the one or more analytes, may be correlated with the administration of the biologically active agent. The change in condition could, for example, indicate that the wearer has received effective treatment with the biologically active agent or not, has developed a disease, disorder, or other adverse medical condition as a result of treatment with the biologically active agent or may be at risk for a severe medical condition, such as a stroke, a heart attack, or diabetic coma, in the near future.

If the server detects a change in condition based on the individual baseline profile and the additional data following administration and conversion of the biologically active agent as discussed above, it may generate one or more recommendations based on the detected change in condition and a clinical protocol (1460). For example, the server may generate a recommendation that the wearer continue or discontinue treatment with the biologically active agent, take a particular medication or supplement, schedule an appointment with a medical professional, go to the hospital to seek immediate medical attention, abstain from certain activities, etc. The server may also be configured to receive data regarding physiological parameters measured by a plurality of wearable devices (1470) and use that data to develop, at least in part, the clinical protocol. The clinical protocol may also be developed based, at least in part, on any known health information or medical history of the wearer, and/or on recognized standards of care in the medical field. The wearable device may receive the one or more recommendations generated by the server (1470) and providing an indication of the one or more recommendations via a user interface on the wearable device.

In some embodiments, the server may be configured to receive data regarding physiological parameters measured by a plurality of wearable devices. The server may use this data collected from a plurality of wearable devices—worn by a plurality of users—to develop, at least in part, a population baseline profile. Such population baseline profiles may be used, for example, for comparison with an individual's baseline profile. Those of skill in the art will readily recognize that comparison of an individual's physiological parameters measured over time to that individual's own baseline may not be sufficient to recognize an abnormality in that physiological parameter. For example, while a physiological parameter for an individual wearer of the device may not deviate from that individual's baseline, that individual baseline may be well above the population baseline generated from data collected from a plurality of wearers of the device. Thus, comparison to what is "normal" or "average" for a population may be necessary for effective identification or prevention of a medical condition in an individual.

Accordingly, the server may further be configured to receive from the wearable device additional data measured during one or more additional measurement periods, detect a change in condition based on the population baseline profile and the additional data, and generate one or more recommendations based on the detected change in condition and a clinical protocol. The wearable device may receive the one or more recommendations generated by the server and provide an indication of the one or more recommendations via a user interface on the wearable device.

Figure 15:
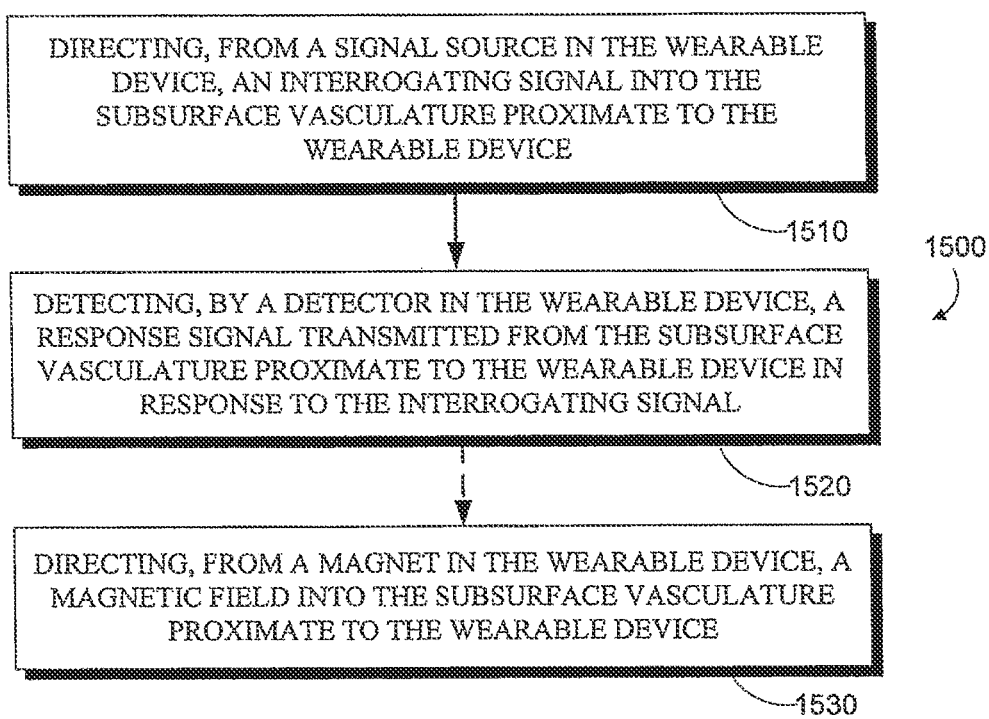
FIG. 15 is a flowchart of an example method for using a wearable device to take real-time, high-density, non-invasive, in vivo measurements of physiological parameters, in particular steps for measuring one or more analytes in blood circulating in subsurface vasculature proximate to the wearable device.

In further embodiments, the method may include introducing functionalized particles into the blood, wherein the functionalized magnetic particles are configured to bind to the one or more analytes. As shown in FIG. 15, the wearable device may non-invasively measure one or more analytes in blood circulating in subsurface vasculature proximate to the wearable device by directing, from a signal source in the wearable device, an interrogating signal into the subsurface vasculature proximate to the wearable device (1510). As discussed above, this step may not be necessary in cases where the functionalized particles generate a response signal related to binding of the one or more analytes without the need for an interrogating signal. In any case, the wearable device may detect, with a detector, a response signal transmitted from the subsurface vasculature proximate to the wearable device in response to the interrogating signal (1520). The response signal is related to binding of the one or more analytes to the functionalized particles. In examples where an interrogating signal is used, the interrogating signal may include a time-varying magnetic field and the response signal may include an externally-detectable physical motion due to the time-varying magnetic field. The interrogating signal may include an electromagnetic pulse (e.g., a radio frequency (RF) pulse) and the response signal may include a magnetic resonance (MR) signal. The interrogating signal may include electromagnetic radiation having a wavelength between about 400 nanometers and about 1600 nanometers, more particularly, a wavelength between about 500 nanometers and about 1000 nanometers. Where the functionalized particles also include a fluorophore, the response signal may include fluorescence radiation transmitted by the fluorophore in response to the interrogating signal.

In some examples, the functionalized particles may also be magnetic. The process of measuring one or more analytes in blood circulating in subsurface vasculature may further include directing, from a magnet in the wearable device, a magnetic field into the subsurface vasculature proximate to the wearable device (1530). The magnetic field is sufficient to cause the functionalized magnetic particles to collect in a lumen of the subsurface vasculature proximate to the wearable device.

Figure 16:
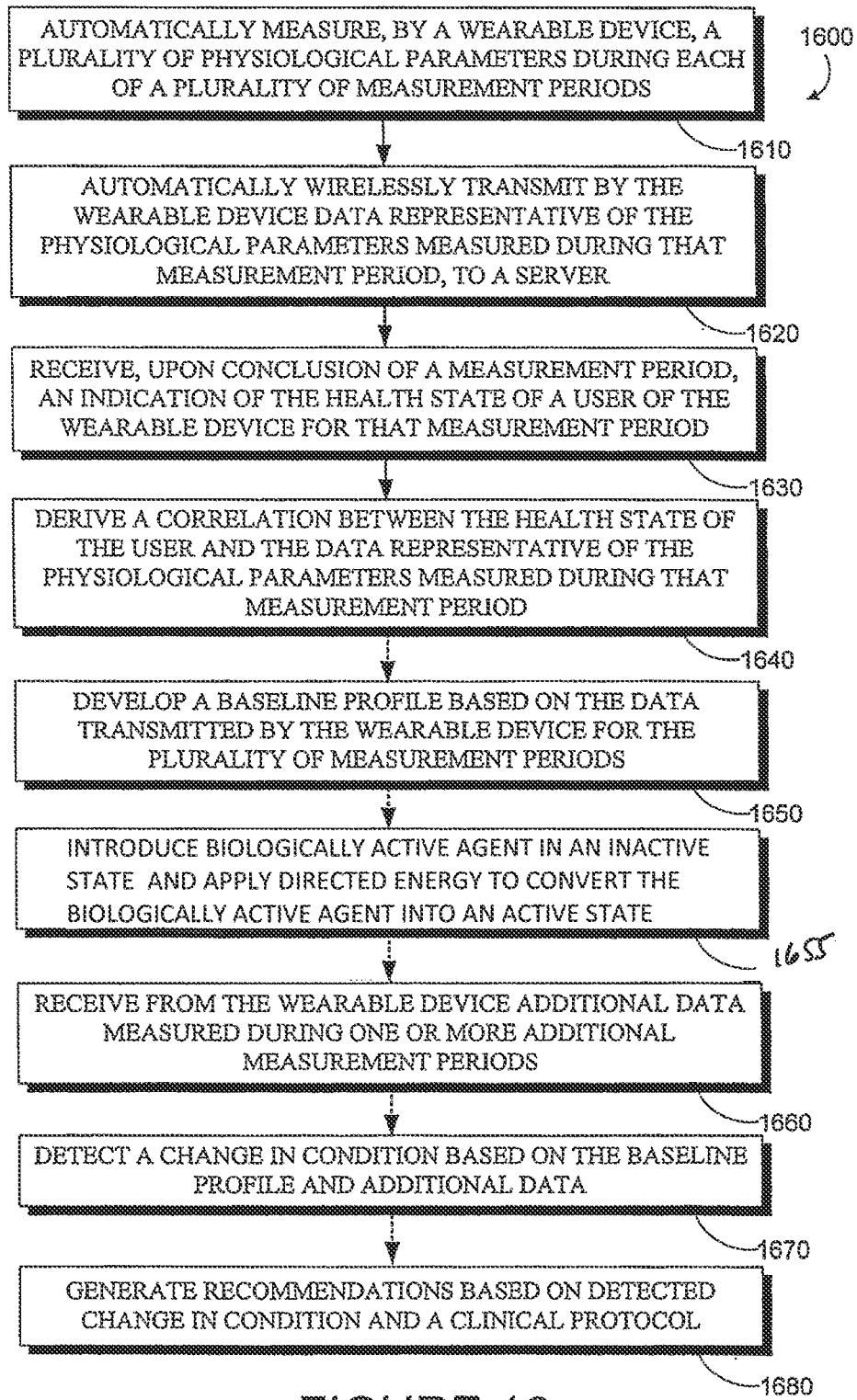
FIG. 16 is a flowchart of an example method for using a wearable device to take real-time, high-density, non-invasive, in vivo measurements of physiological parameters.

FIG. 16 is a flowchart of a method 1600 for using a wearable device to take real-time, high-density, non-invasive, in vivo measurements of physiological parameters. In a first step, the wearable device automatically measures one or more physiological parameters during each of a plurality of measurement periods (1610). The measurement periods may extend through a plurality of consecutive days, wherein each of the consecutive days includes multiple measurement periods. At least some of the physiological parameters are measured by non-invasively detecting one or more analytes in blood circulating in subsurface vasculature proximate to the wearable device.

Upon conclusion of a measurement period for each of the plurality of measurement periods, the wearable device automatically wirelessly transmits to a server data representative of the physiological parameters measured during that measurement period (1620). The server may be configured to receive, upon conclusion of a measurement period, an indication of the health state of a user of the wearable device for that measurement period and derive a correlation between the health state of the user and the data representative of the physiological parameters measured during that measurement period (1630). For example, the server may be configured to recognize patterns, for example, every time a physiological parameter reaches or drops to a certain level, the wearer of the device indicates that he or she experiences a migraine. Recognition of these patterns or correlations may help medical professionals to recognize, prevent, diagnose and/or treat of health conditions in that individual. Further, the server may be configured to use these correlations to alert the user that a medical condition may be imminent.

A baseline profile may be developed by the server based on the data transmitted by the wearable device for the plurality of measurement periods (1650). The biologically active agent in an inactive state may be administered (1655) to the wearer by any suitable means including ingestion, injection or infusion. Directed energy is then applied to the tissue from an external surface of the wearer's body to convert the biologically active agent from the inactive state to the active state (1655). The server may further be configured to receive from the wearable device additional data representative of the physiological parameters measured during one or more additional measurement periods (1660), detect a change in condition based on the baseline profile and the additional data (1670) as a result of administering the biologically active agent in its active state, and generate one or more recommendations based on the detected change in condition and a clinical protocol (1680). The detectable changes in the wearer's condition as determined, for instance, by changes in the presence or absence of one or more target analytes or changes in the concentrations or abundance of the one or more analytes, may be correlated with the administration of the biologically active agent. The clinical protocol may be developed based, at least in part, on the derived correlation. For example, the clinical protocol may indicate that the drug treatment may or may not be effective and a worsening of the medical condition or wearer's health state may be imminent based on a comparison between current measurement of a physiological parameter and the derived correlation between previously measured physiological parameters and previously reported health state.

In a further example, the server may be configured to receive data regarding physiological parameters measured by a plurality of wearable devices and receive an indication of the health state of the users of the plurality of wearable devices for a plurality of measurement periods. The server may then derive a correlation between the health state of the users and the data representative of the physiological parameters measured during the plurality of measurement periods. Population data of this kind may be significant in that such correlations may never before have been drawn between that physiological parameter and a particular health condition. Such correlations may be used in prediction, prevention, diagnoses and treatment of health conditions. The server may also be configured to receive from the wearable device additional data representative of the physiological parameters measured during one or more additional measurement periods and generate one or more recommendations based on the received additional data and a clinical protocol, wherein the clinical protocol is developed based, at least in part, on the derived correlation.

In a further example, the wearable device itself may be configured to perform the steps described above as being performed by a remote server. For example, the wearable device may be configured to analyze the data representative of the physiological parameters, generate a baseline profile, compare data collected from additional measurement periods to the baseline profile, and generate recommendations based on a clinical protocol. The wearable device may further be configured to transmit, either automatically or on some other frequency, certain data to the remote server.

VII. CONCLUSION

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. A system comprising:
    a wearable device for detecting an analyte response signal and an unbound functionalized particle signal from tissue through an external surface of a living body, the wearable device comprising a mount adapted for mounting the wearable device on the external surface of a living body and a detector,
        wherein the tissue contains a biologically active agent in an inactive state and functionalized particles, wherein the functionalized particles can interact with one or more target analytes, wherein the biologically active agent can be converted from the inactive state to an active state, wherein the concentration or abundance of the one or more target analytes is correlated with a biological state of the living body that is affected by the biologically active agent when in the active state, wherein the analyte response signal is related to interaction of the one or more target analytes with the functionalized particles, and wherein the unbound functionalized particle signal is related to functional particles that are not interacting with the one or more target analytes;
    a directed energy source;
    a modulation source;
    a processor; and
    a computer readable medium storing instructions executable by the processor to perform operations comprising:
        controlling the directed energy source to apply directed energy into the tissue through the external surface, wherein the directed energy is sufficient to convert the biologically active agent from the inactive state to the active state;
        controlling the detector to detect an analyte response signal transmitted from tissue through the external surface;
        controlling the modulation source to modulate the analyte response signal and the unbound functionalized particle signal, such that the analyte response signal is affected differently than the unbound functionalized particle signal; and
        controlling the processor to determine the concentration or abundance of the one or more target analytes by differentiating the analyte response signal from the unbound functionalized particle signal, based, at least in part, on the modulation.

2. The system of claim 1, wherein the biologically active agent comprises a pro-drug when in the inactive state and comprises a drug when in the active state.

3. The system of claim 1, wherein the biologically active agent is associated with a carrier when in the inactive state and is released from the carrier when in the active state.

4. The system of claim 3, wherein the carrier comprises a liposome, micelle, nanoparticle, nanocage or reservoir.

5. The system of claim 1, wherein the directed energy comprises electromagnetic radiation, acoustic energy, or heat.

6. The system of claim 5, wherein the directed energy comprises a series of one or more pulses for controlling a rate of conversion of the biologically active agent from the inactive state to the active state.

7. The system of claim 6, wherein the operations further comprise controlling the rate of conversion based on the determined concentration or abundance of the one or more target analytes.

8. The system of claim 1, wherein the operations further comprise assessing an effect of the biologically active agent on the biological state of the living body based on the determined concentration or abundance of the one or more target analytes.

9. The system of claim 1, wherein the directed energy is applied in response to the determined concentration or abundance of the one or more target analytes.

10. The system of claim 1, wherein the operations further comprise differentiating the analyte response signal from a background signal based, at least in part, on the modulation by the modulation source.

11. The system of claim 1, further comprising an interrogating signal source, wherein the analyte response signal is transmitted in response to an interrogating signal transmitted into the tissue by the interrogating signal source.

12. The system of claim 11, wherein the analyte response signal is modulated by modulating the interrogating signal.

13. The system of claim 1, wherein the tissue comprises subsurface vasculature, and wherein the biologically active agent and functionalized particles are in blood circulating in the subsurface vasculature.

14. The system of claim 1, wherein the wearable device further comprises the directed energy source.

15. A method comprising:
    introducing a biologically active agent in an inactive state into a living body, wherein the biologically active agent can be converted to an active state that affects a biological state of the living body;

introducing functionalized particles into the living body, wherein the functionalized particles can interact with one or more target analytes, wherein concentration or abundance of the one or more target analytes in the living body is correlated with the biological state of the living body;

applying directed energy into the living body, wherein the directed energy is sufficient to convert the biologically active agent in the living body from the inactive state to the active state;

detecting, by a wearable device mounted on an external surface of the living body, a signal transmitted from the living body, wherein the signal includes an analyte response signal that is related to interaction of the one or more target analytes with the functionalized particles and an unbound functionalized particle signal that is related to functionalized particles that are not interacting with the one or more target analytes;

applying a modulation into the living body, wherein the modulation can alter the analyte response signal and the unbound functionalized particle signal, such that the analyte response signal is affected differently than the unbound functionalized signal, and differentiating the analyte response signal from the unbound functionalized particle signal and determining concentration or abundance of the one or more target analytes based on the analyte response signal.

16. The method of claim 15, wherein the directed energy is applied by the wearable device.

17. The method of claim 15, wherein the concentration or abundance of the one or more target analytes is determined after applying the directed energy, further comprising:
assessing an effect of the biologically active agent on the biological state of the living body based on the determined concentration or abundance of the one or more target analytes.

18. The method of claim 15, wherein the concentration or abundance of the target analyte is determined before applying the directed energy, and wherein the directed energy is applied in response to the determined concentration or abundance of the one or more target analytes.

19. The method of claim 15, wherein the biologically active agent comprises a pro-drug when in the inactive state and comprises a drug when in the active state.

20. The method of claim 15, wherein the biologically active agent is associated with a carrier when in the inactive state and is released from the carrier when in the active state.

21. The method of claim 15, wherein the directed energy comprises electromagnetic radiation, acoustic energy, or heat.

22. The method according to claim 15, further comprising differentiating the analyte response signal from a background signal.

* * * * *